(12) United States Patent
Hoess et al.

(10) Patent No.: US 7,897,404 B2
(45) Date of Patent: Mar. 1, 2011

(54) CONJUGATES OF DEFINED STOICHIOMETRY

(75) Inventors: Eva Hoess, Munich (DE); Herbert Andres, Penzberg (DE); Frederic Donie, Penzberg (DE); Rudolf Vogel, Weilheim (DE); Hans-Peter Josel, Weilheim (DE); Rupert Hermann, Weilheim (DE); Herbert Von Der Eltz, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 10/381,941

(22) PCT Filed: Aug. 26, 2001

(86) PCT No.: PCT/EP01/11101
§ 371 (c)(1),
(2), (4) Date: Nov. 17, 2003

(87) PCT Pub. No.: WO02/27317
PCT Pub. Date: Apr. 4, 2002

(65) Prior Publication Data
US 2004/0087501 A1 May 6, 2004

(30) Foreign Application Priority Data

Sep. 29, 2000 (DE) .................................. 100 48 417
Mar. 29, 2001 (EP) ..................................... 01107491

(51) Int. Cl.
*G01N 30/02* (2006.01)
(52) U.S. Cl. ......... 436/161; 73/61.52; 210/656; 435/7.1; 435/961; 435/962; 436/544
(58) Field of Classification Search .................. 436/518, 436/524–534, 56, 73, 84, 161, 174–178; 435/803; 210/656, 660; 424/1.73, 9.6; 525/50, 525/54.1
See application file for complete search history.

(56) References Cited

U.S. PATENT DOCUMENTS

| | | | |
|---|---|---|---|
| 2,493,382 A * | 1/1950 | Bell | 141/130 |
| 5,047,324 A | 9/1991 | Fredrickson | |
| 5,554,748 A * | 9/1996 | Sieving et al. | 540/465 |
| 5,958,783 A * | 9/1999 | Josel et al. | 436/84 |
| 6,120,768 A | 9/2000 | Griffiths et al. | |
| 6,491,903 B1 * | 12/2002 | Forster et al. | 424/78.01 |

FOREIGN PATENT DOCUMENTS

| | | |
|---|---|---|
| EP | 0 061 888 B1 | 3/1982 |
| WO | WO 96/03409 | 2/1996 |
| WO | WO 96/03423 | 2/1996 |
| WO | WO 96/03651 A1 | 2/1996 |
| WO | WO 96/03652 | 2/1996 |
| WO | WO 96/03657 | 2/1996 |

OTHER PUBLICATIONS

Regnier FE. High-performance liquid chromatography of biopolymers. Science. 1983;222:245-252.*
Tijssen, "Preparation of enzyme-antibody or other enzyme-macromolecule conjugates" Labor Techn. (1985) 11: pp. 221-278.
Engval A. Perlmann, "Enzyme-linked immunosorbent assay (ELISA) Quantitative assay of immunoglobulin G" Immunochemistry (1971) 8: pp. 871-874.
A. Merzouk and F. Guibe, "*On the Use of Silylated Nucleophiles in the Palladium Catalysed Deprotection of Allylic Carboxylates and Carbamates*" Tetrahedron Letters (1992) vol. 33 No. 4. pp. 477-480.
Sun-Sun Wang, "*p-Alkoxybenzyl Alcohol Resin and p-Alkoxybenzyloxycarbonylhydraxide Resin for Solid Phase Synthesis of Protected Peptide Fragments*" Journal of the American Chemical Society (1973) 95:4 pp. 1328-1333.
Bycroft, et al. "*A Novel Lysine-Protecting Procedure for Continuous Flow Solid Phase Synthesis of Branched Peptides*" J. Chem. Soc. Chem. Commun. (1993) pp. 778-779.
Van Weemen et al., "*Immunoassay Using Antigen-Enzyme Conjugates*" FEBS Letters (1971) 15:3 pp. 232-236.

* cited by examiner

*Primary Examiner* — Melanie J. Yu
*Assistant Examiner* — Gary W Counts

(57) ABSTRACT

The invention relates to a process for the production of a biomolecule-linker conjugate of uniform stochiometry. It especially relates to a conjugate consisting of a biomolecule of a molecular weight between 5 kD and 500 kD and a hydrophilic linker molecule said linker having a molecular weight between 1 and 15 kD and between 4 and 60 charged residues, characterized in that said conjugate comprises at least one biomolecule-linker product of uniform stoichiometry in a pre-selected amount.

14 Claims, 11 Drawing Sheets

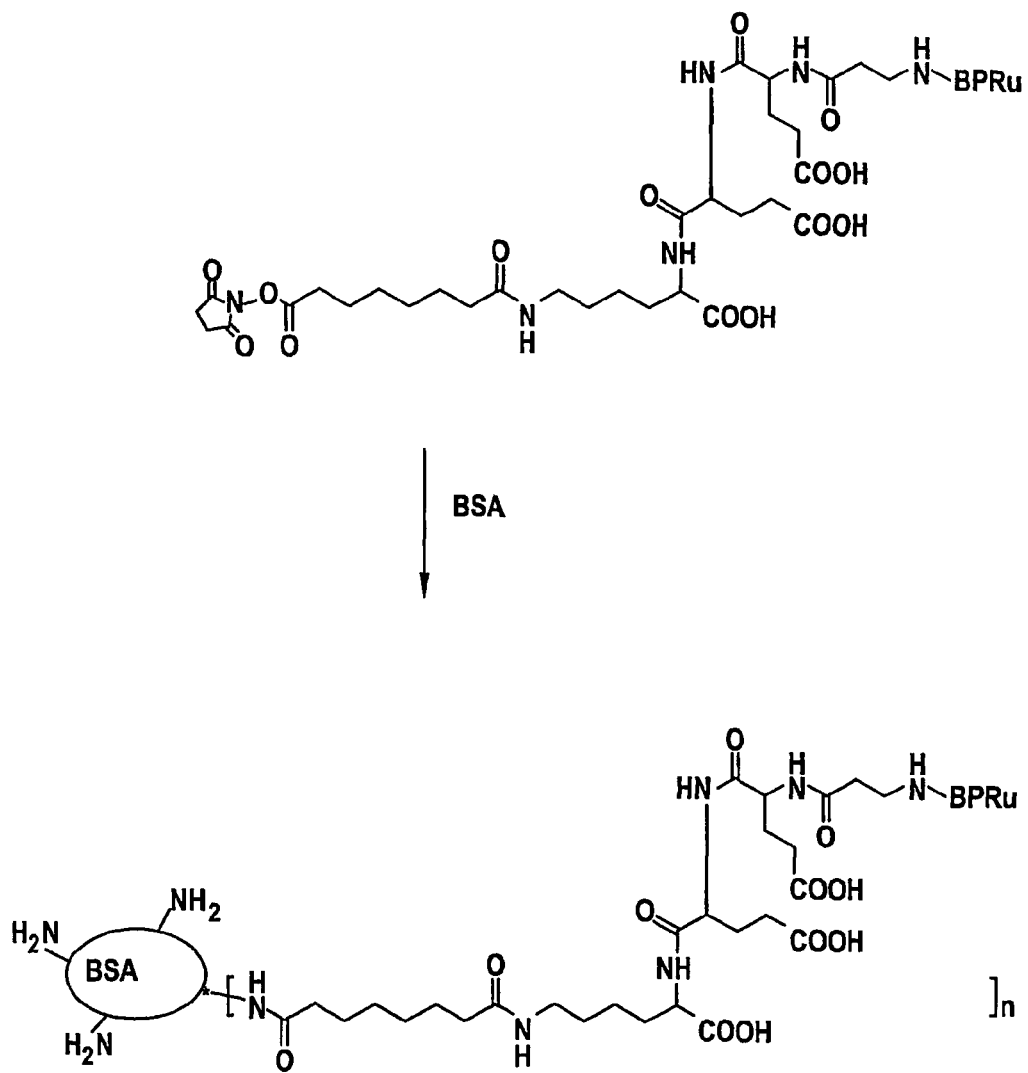
Figure 1: Schematic for BSA and its conjugation to hy-BPRu

Figure 2: Superdex 200 HR® chromatograph of a BSA-hy-BPRu-conjugate
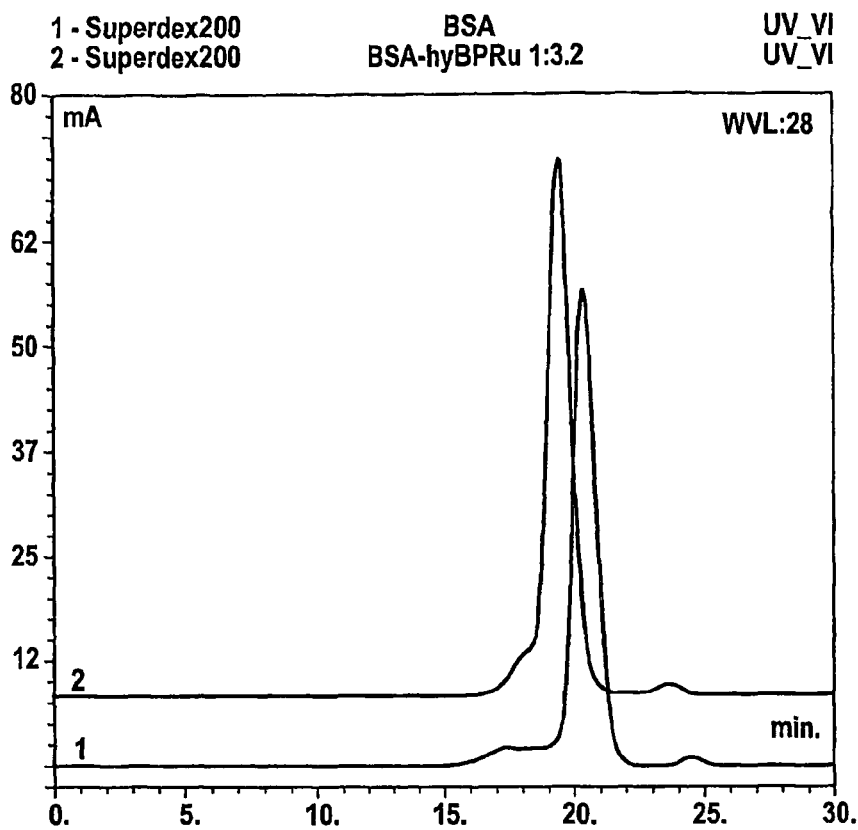
Figure.3: Schematic of BPRu-(UE)$_{25}$K and BPRu-(UE)$_{50}$K
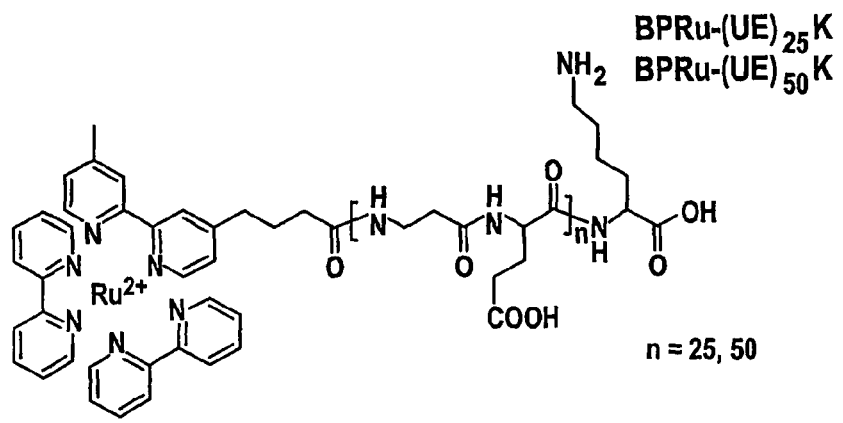

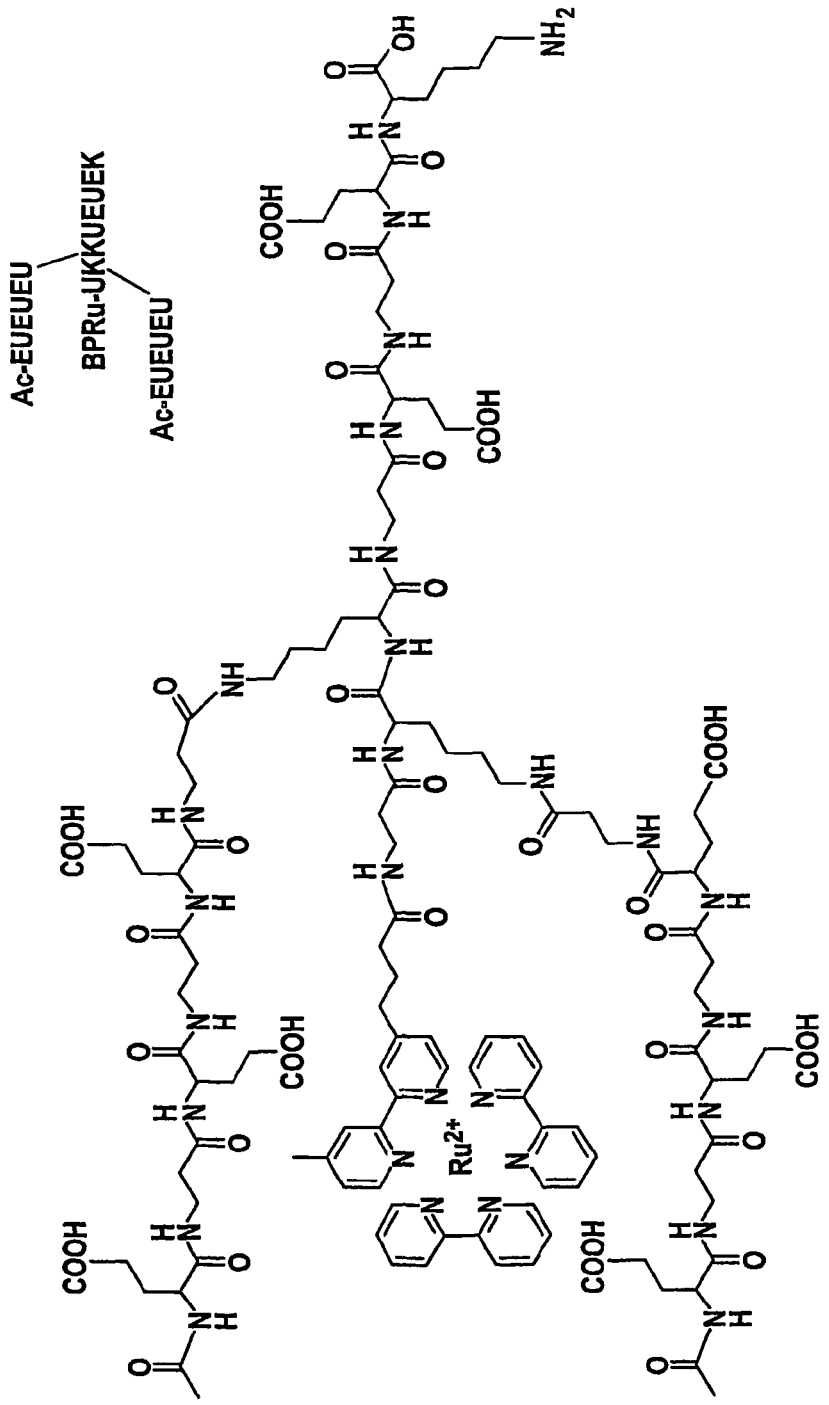
Figure 4: Branched linker with short backbone chain

Figure 5: Branched linker with long backbone chain
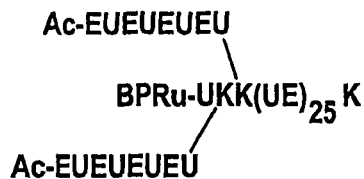
Figure 6: Schematic of a branched linker without charged residues
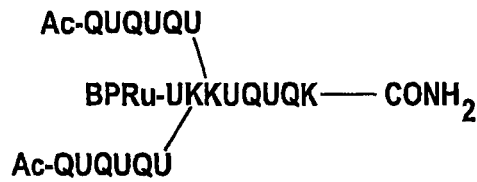
Figure 7: Schematic of biotinylated linker molecules
Bi-(UE)$_{25}$-K-MH
Bi-(UE)$_{25}$-K-DSS
Figure 8: Schematic of a multiply branched linker with two marker groups
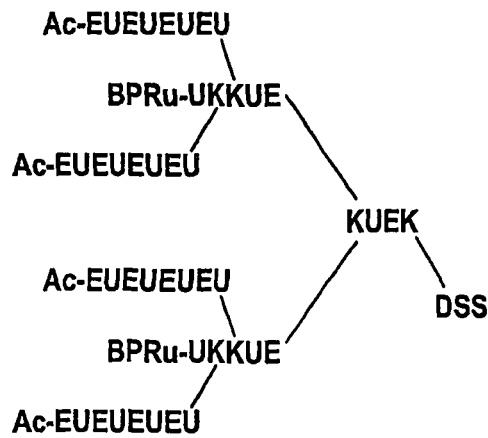

Figure 9: Superdex 200 HR® chromatography of various linker molecules
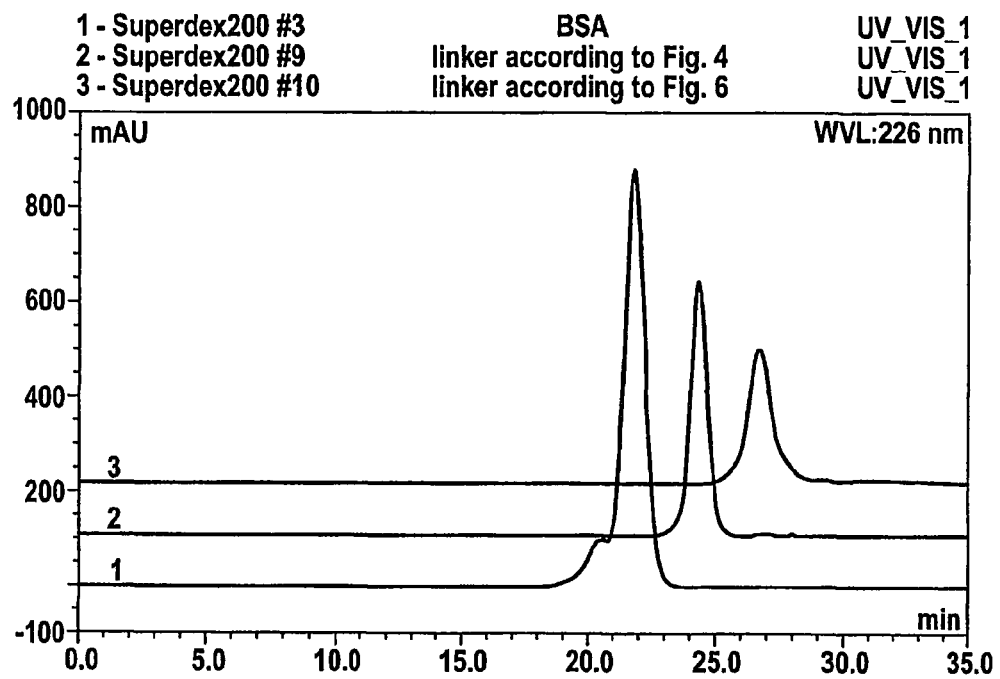
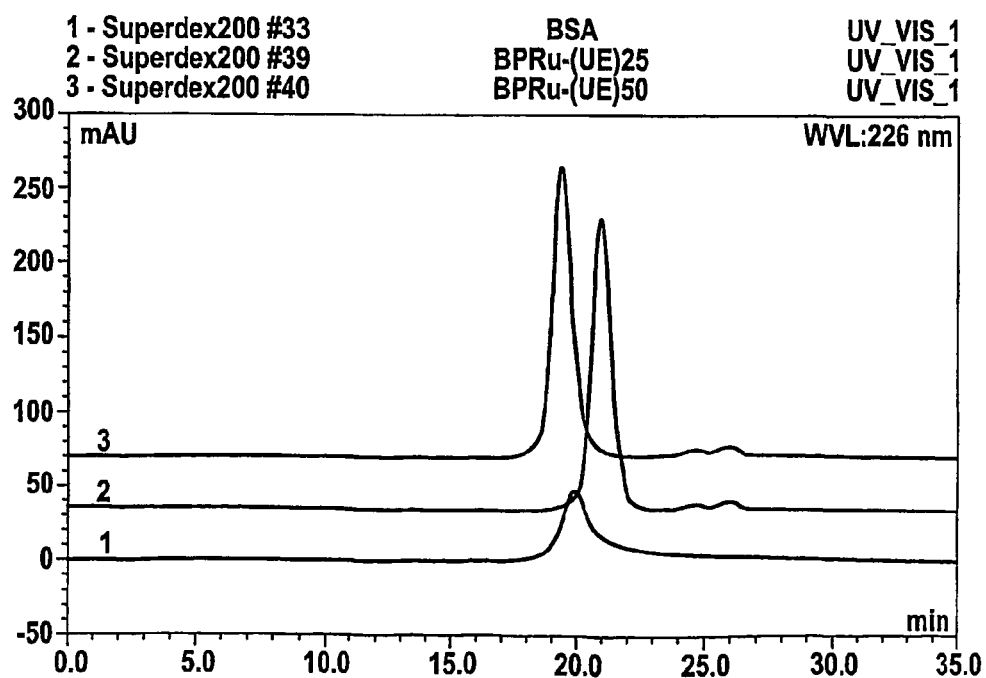

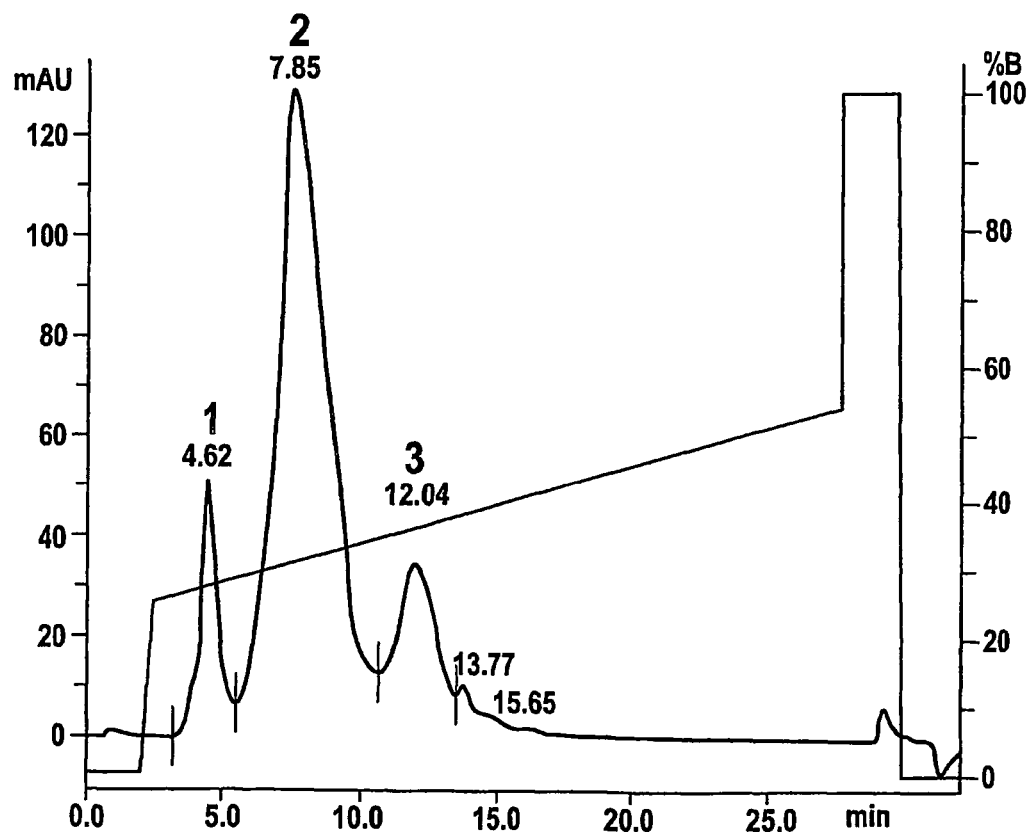
Figure 10: Mono Q® chromatograph of a crude BSA-Ru(SK)$_4$-MH conjugate

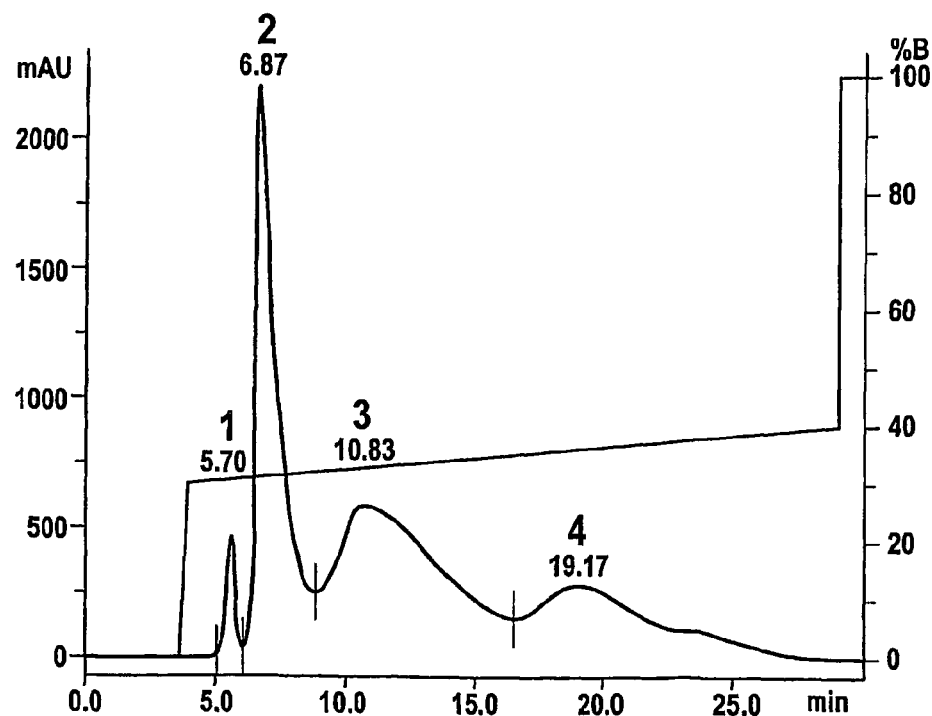
Figure 11: Source 15 Q® chromatograph of a crude BSA-Ru(UE)$_{25}$-MH conjugate

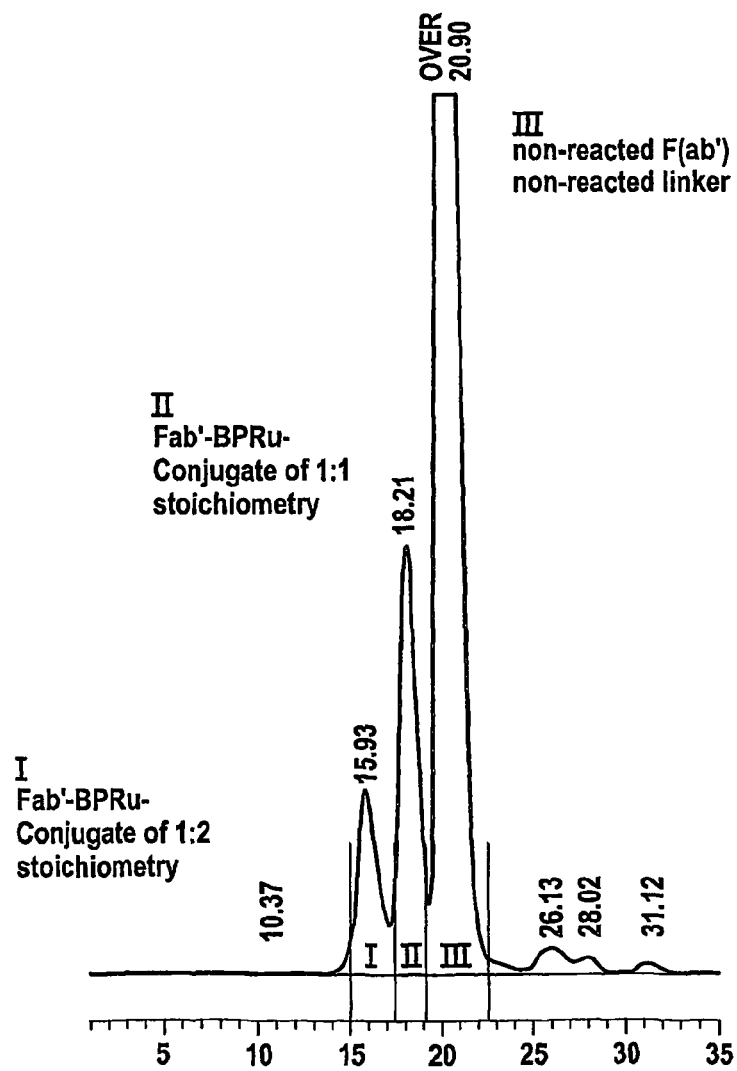
Figure 12: Superdex 200 HR® 10/30 chromatograph of a first Fab'-Ru(UE)$_{25}$-MH coupling product

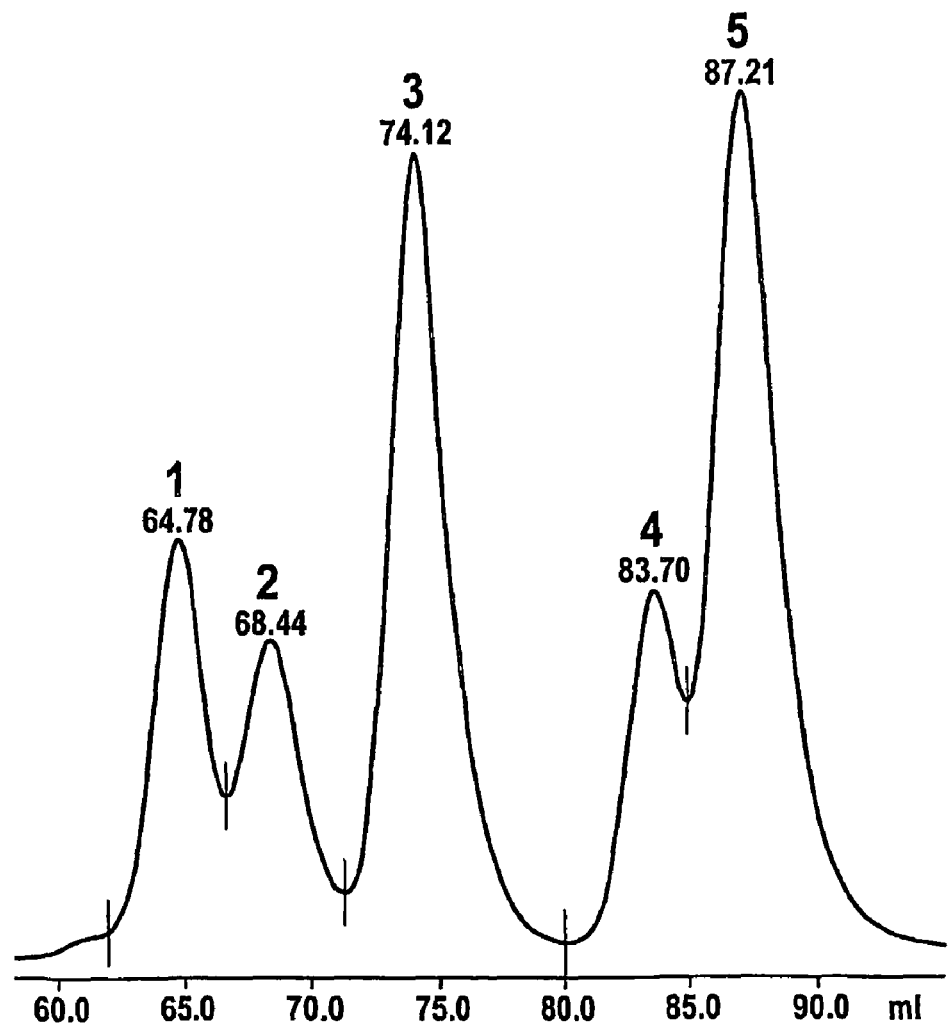
Figure 13: Superdex 200 HR® 10/30 chromatograph of a second Fab'-Ru(UE)$_{25}$ coupling product.

Figure 14: Purification of F(ab')$_2$-BPRu-(UE)$_{25}$-DSS coupling products
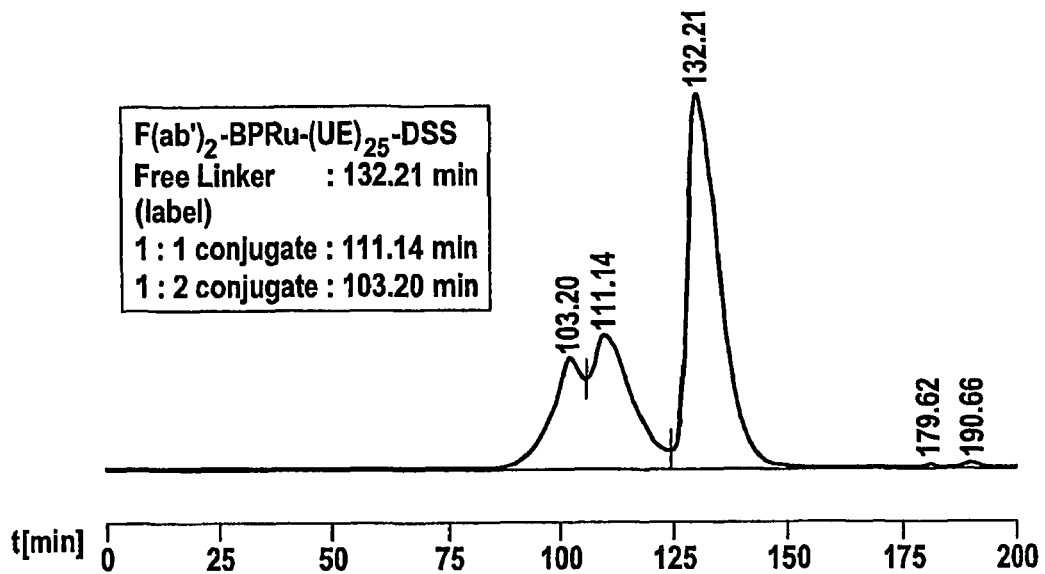
Figure 15: Purification of F(ab')$_2$-BPRu-UEEK-DSS coupling products
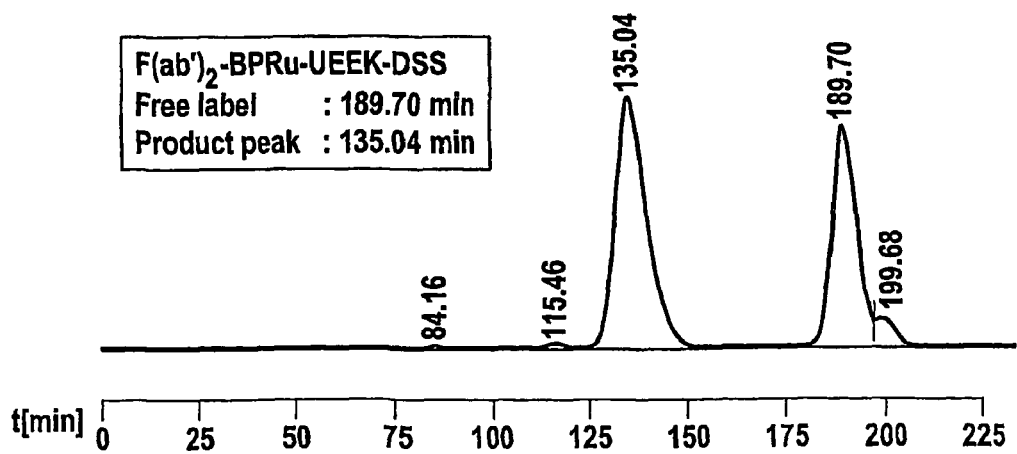

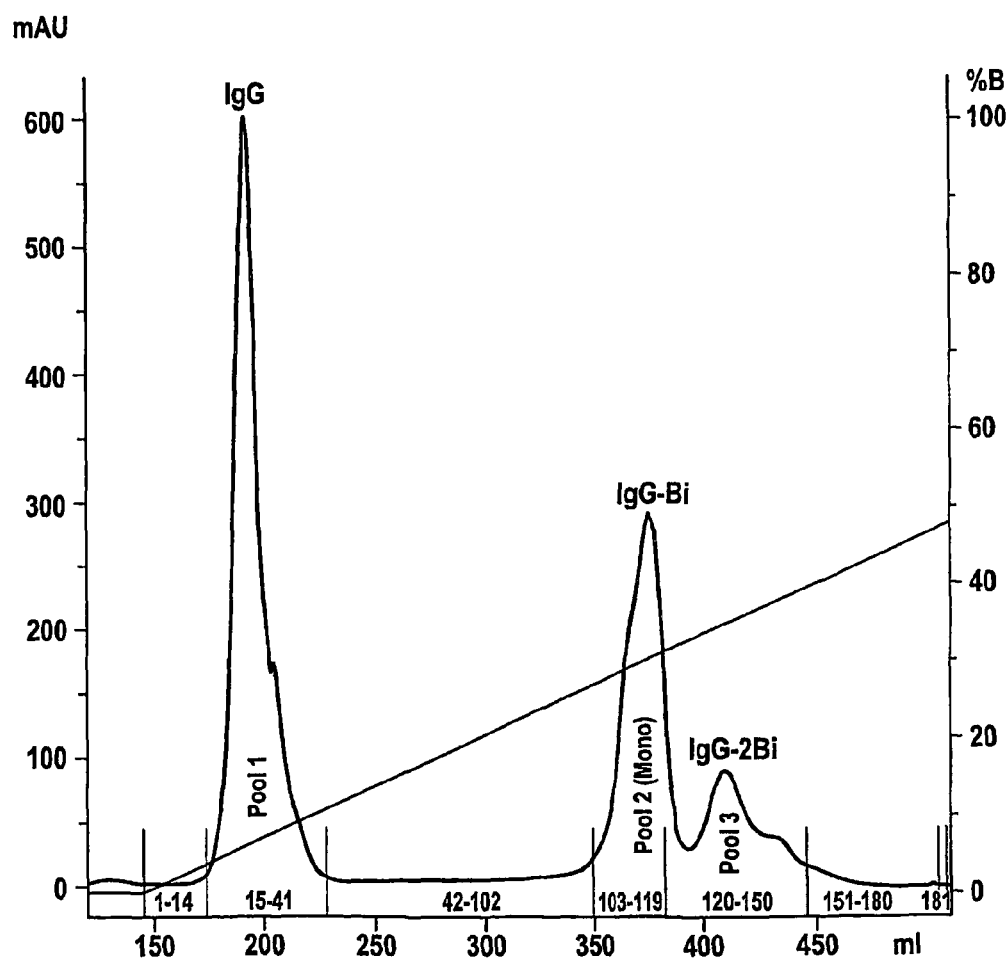
Figure 16: Purification of IgG-(Bi-(UE)$_{25}$-DSS) coupling products

CONJUGATES OF DEFINED STOICHIOMETRY

The invention relates to a process for the production of a biomolecule-linker conjugate of uniform stoichiometry. It especially relates to a conjugate consisting of a biomolecule of a molecular weight between 5 kD and 500 kD and a hydrophilic linker molecule, said linker having a molecular weight between 1 and 15 kD and between 4 and 60 charged residues, characterized in that said conjugate comprises at least one biomolecule-linker product of uniform stoichiometry in a pre-selected amount.

Binding assays nowadays are widely used in research settings as well as in clinical settings, especially in diagnosing an infection, monitoring of drugs, or for assessing normal or abnormal metabolism.

The use of binding assays dates back about 30 years (Engvall, E. and Perlman, P., Immunochemistry 8 (1971) 871-4; van Weemen, B. K. and Schuures A. H. W. M. (1971), FEBS letters 15, 232). Since then, enormous progress has been made and methods for carrying out specific binding assays, as well as practical applications thereof, have become well known to the skilled artisan. Methods and procedures summarized in related text books are herewith included by reference and only few examples shall be specifically mentioned: "Practice and theory of enzyme immunoassays" by Tijssen— in "Methods in Enzymology" (1992) Academic Press; and various editions of "Methods in Enzymology", Colowick S. P., Caplan N. O., Eds., Academic Press, dealing with immunological detection methods, especially volumes 70, 73, 74, 84, 92 and 121.

With the exception of very few homogeneous or precipitation type assays, all these assays require conjugates between a biomolecule, e.g. an antibody, with a second molecule necessary to facilitate the measurement of an analyte under investigation. Well-known examples for this second molecule, e.g., are marker or label groups, like enzymes, radio isotopes, luminophores, fluorphores, etc. or haptens.

Conjugates between a biomolecule and e.g. a marker or hapten group can be synthesized by direct chemical coupling of the two different molecular entities or by using a linker or bridging molecule according to state of the art procedures (e.g. Tijssen or Methods in Enzymology, supra).

Conventional conjugates, however, have clear-cut-limitations. It is a well-known problem that the two or three components of such conjugates, i.e. the biomolecule, the linker (if present), and the marker group may mutually and adversely effect each other. This frequently leads to aggregation or background problems.

Depending on the coupling or linker chemistry chosen, in many cases e.g. amino acid groups of polypeptide which do not end up carrying a marker group, are also modified. This again leads to unpredictable results and through changes in the physico-chemical properties of the biomolecule, to problems like e.g. instability, aggregation or to non-specific binding in immunoassays.

The various components of such a conjugate, e.g., the biomolecule, the linker molecule, and the marker molecule, as well as the different coupling products derived thereof, are present in statistical amounts. A mere statistical mixture with an average labeling index is obtained. The average labeling index may be controlled to some extend by adjusting the reaction conditions and ratios of the individual molecular entities chosen.

Such statistical mixtures comprise a lot of different conjugation products in different stoichiometries. Biomolecules completely free of a linker or marker structure, conjugates of a 1:1 stoichiometry, 1:2 stoichiometry (i.e. a biomolecule carrying 2 linker or marker molecules, 1:3 stoichiometry and even higher stoichiometry may be present in such conjugates. It is obvious that not all such products are desired and cause problems e.g. with respect to reproducibility of conjugation. In addition, non-labeled biomolecules interfere with labeled biomolecules. It is also known that "over-labeling", i.e. biomolecules labeled with too many hapten or marker structures, is the major reason for problems known as non-specific interactions, e.g. background phenomena.

U.S. Pat. No. 5,958,783 discloses that it is possible to reduce background problems caused by a metal chelate complex as marker group by using a hydrophilic linker entity. However, the conjugates according to U.S. Pat. No. 5,958,783 still represent statistical mixtures of various different biomolecule-linker-marker products. Reproducibility of these statistical conjugates still remains a problem.

WO 96/03423 and WO 96/03651 describe that it is possible to introduce marker groups at predetermined positions during synthesis. This way it is possible to synthesize a peptide-linker (marker) product of uniform stoichiometry. However, the limits of peptide synthesis are in the range of 40 to 50 amino acids corresponding to peptides of a molecular weight below 5 kD (kD=kilo Dalton). Polypeptides of more than 5 kD usually are produced by recombinant expression in appropriate host systems and need to be chemically coupled resulting in a conjugate of statistical compositions. The linkers of WO 96/03423 and WO 96/03657 are below 1 kD and do not contain charged residues.

Large biomolecules, e.g. polypeptides of 40 to 50 amino acids usually contain more than one reactive group amenable to one of the standard coupling chemistries.

The mode and strategy of chemical coupling can be selected as required. In cases where the biomolecule is a polypeptide, coupling chemistries targeting —SH, —$NH_2$ or —$COO^-$ residues as well as the —OH group of tyrosines, the imidazol group of histidines or the heterocyclic imino groups of tryptophanes can be used. Several appropriate coupling chemistries are known from the art for each of these functional groups (Aslam, M. Dent, A. The preparation of protein-protein conjugates in "Bioconjugation" (1998) 216-363, London, McMillan).

Whenever more than one reactive group is present on a biomolecule chemical, coupling with a linker or marker results in a statistical mixture of different biomolecule-linker or biomolecule-marker products.

Even with the most advanced linkers and coupling chemistries, the resulting conjugate is a statistical mixture of many different conjugates and the overall result of such conjugation is highly variable and unpredictable. As a consequence, it is very difficult to reproduce the overall properties of such conjugates from lot to lot.

It was therefore the task of the present invention to investigate whether a conjugate between a biomolecule and a linker molecule could be prepared in a more reproducible and defined manner. It was also investigated whether it was possible to obtain a conjugate comprising at least one pre-selected biomolecule-linker product of uniform stoichiometry.

Surprisingly, it has been found that problems known in the art can be overcome by the conjugates according to the present invention, their mode of production and their use in appropriate reagents, kits and procedures.

Disclosed is a process for the production of a conjugate comprising at least one biomolecule-linker product of uniform stoichiometry in a pre-selected amount, said conjugate consisting of a biomolecule of a molecular weight between 5 kD and 500 kD and a hydrophilic linker molecule, said linker having a molecular weight between 1 kD and 15 kD and containing between 4 and 60 charged residues, where the method is characterized by a) the biomolecule and the linker molecule are covalent coupled to each other, b) the different biomolecule-linker products of uniform stoichiometry are fractionated by chromatography, and c) fractions containing a coupling product of uniform stoichiometry are collected.

The invention also relates to a conjugate consisting of a biomolecule of a molecular weight between 5 kD and 500 kD and a hydrophilic linker molecule, said linker having a molecular weight between 1 and 15 kD and between 4 and 60 charged residues. The conjugate is further characterized in that it comprises at least one biomolecule-linker product of uniform stoichiometry in a pre-selected amount.

The conjugates according to the present invention are especially useful for performing a biochemical or immunological assay for detection of an analyte in a sample. The invention therefore also relates to a composition of reagents comprising the described conjugate, a test kit comprising such a conjugate as part of a reagent composition and to an immunoassay based on such a conjugate.

DETAILED DESCRIPTION OF THE INVENTION

A preferred embodiment of the present invention is a process for the production of a conjugate comprising at least one biomolecule-linker product of uniform stoichiometry in a pre-selected amount, said conjugate consisting of a biomolecule of a molecular weight between 5 kD and 500 kD and a hydrophilic linker molecule, said linker having a molecular weight between 1 kD and 15 kD, between 4 and 60 charged residues, characterized in that
  a) the biomolecule and the linker molecule are covalent coupled to each other,
  b) the different biomolecule-linker products of uniform stoichiometry are fractionated by chromatography, and
  c) fractions containing a coupling product of uniform stoichiometry are collected.

The term "conjugate" is used to describe a coupling product between a biomolecule and a linker molecule. A conjugate according to the present invention comprises at least one biomolecule-linker product of uniform stoichiometry in a pre-selected amount.

Biomolecule in the sense of the present invention may be any naturally occurring or synthetically produced molecule with a molecular weight between 5 and 500 kD composed of biological molecules like amino acids, nucleotides, nucleosides, lipids, and/or sugars. Preferably, the biomolecule is selected from the group consisting of polypeptides, polysaccharides, and lipopolysaccharides. Preferably the biomolecule has a molecular weight in the range of 10 kD to 500 kD. More preferred the biomolecule has a molecular weight in the range of 15 kD to 400 kD, most preferred in the range of 20 kD to 200 kD.

The biomolecule preferably has at least two groups that are amenable to standard coupling chemistry. Examples of such groups are known in the art as reactive groups, functional groups, or coupling sites are described further below.

In a preferred embodiment, the biomolecule is a polypeptide. Preferably such polypeptide comprises 50 to 5000 amino acids, or more preferred 100 to 4000 amino acids.

The linker according to the present invention has a molecular weight of 1 kD to 15 kD and carries at least four charged residues. The molecular weight range given applies for the basic linker molecule without active groups or marker groups.

The molecular weight of the linker is at least 1000 D. The molecular weight of the linker is preferably in the range of 1000 to 15,000 D, particularly in the range of 1000 to 12,000 D and most preferably in the range of 1000 to 10,000 D. Also preferred are molecular weight ranges for the linker molecule between 1500 and 15000 D and also between 1500 and 10000 D.

Preferably the linker used to produce the conjugate according to the present invention comprises a peptidic backbone.

In the sense of the present invention, the term "charge carrier" means a group which is present mainly in an ionic form at a pH value in the range from 6 to 8. The linker preferably contains 4 to 60, particularly preferred 6 to 50 and most preferred 9 to 40 such charge carriers.

It is preferred that all charge carriers are either positively or negatively charged. It is, however, also possible to use linker molecules which carry both, positively and negatively charged residues. In such a case, the number of positively charged residues is either higher or lower by at least four as compared to the number of negatively charged residues.

The linker preferably comprises at least four negative charge carriers. Examples of suitable negative charge carriers are phosphate, phosphonate, sulphinate, sulphonate, sulphate and carboxylate groups. Carboxylate groups and phosphate groups being most preferred.

It is further preferred, that the linker comprises at least four positively charged residues. Examples of positive charge carriers are amino and mono-substituted or poly-substituted amino groups such as mono, di- or trialkyl amino groups, in which alkyl denotes a straight-chained or branched alkyl residue with 1 to 6 C atoms or a cyclic alkyl residue with 3 to 6 C atoms, guanidinyl groups, e.g. of arginine or positively charged heteroaromatic nitrogen groups, as, e.g. found in histidine. The positive charge carriers preferably are selected from basic amino acids such as lysine or substituted amino acids such as diethyllysine.

The linkers can also contain uncharged hydrophilic groups as an alternative to, or in addition to, the charge carriers. Preferred examples of uncharged hydrophilic groups are ethylene oxide or polyethylene oxide groups with preferably at least three ethylene oxide units, sulphoxide, sulphone, carboxylic acid amide, carboxylic acid ester, phosphonic acid amide, phosphonic acid ester, phosphoric acid amide, phosphoric acid ester, sulphonic acid amide, sulphonic acid ester, sulphuric acid amide and sulphuric acid ester groups. The amide groups are preferably primary amide groups, particularly preferably carboxylic acid amide residues in amino acid side groups e.g. the amino acids asparagine and glutamine. The esters are preferably derived from hydrophilic alcohols, in particular $C_1$-$C_3$ alcohols or diols or triols.

The linker according to the present invention preferably is modified to carry additional chemical structures. Most preferably, such modified linker is of the formula ($Z$-$L$-$X_n$) and comprises one group Z and one or several groups X (n=1-10), wherein L is the core structure of said linker.

The reactive group Z is used for chemically coupling the linker to the biomolecule. The group Z is preferably an activated carboxylic acid group such as a carboxylic acid halogenide, a carboxylic acid anhydride, a carboxylic acid hydrazide, a carboxylic acid azide or an active ester e.g. an N-hydroxy-succinimide, a p-nitrophenyl, pentafluorophenyl, imidazolyl or N-hydroxybenzotriazolyl ester, an amine, a maleimide, a thiol, a para-aminobenzoyl group or a photoactivatable group e.g. an azide.

The X group is either a reactive group as defined for Z above, or X is a marker group. In case X is a reactive group it is present only once and the linker is a heterobifunctional linker. The skilled artisan has no difficulty in selecting appropriate combinations of reactive groups for X and for Z.

Examples for appropriate active groups in heterobifunctional linkers are e.g. given in Aslam, M. Dent, A. The preparation of protein-protein conjugates in "Bioconjugation" (1998) 216-363, London, McMillan or in Tijssen Laboratory techniques in "Macromolecule conjugation" (1985) 258-268. In case X is a marker group it is present up to ten times, preferably up to four times. Also preferred the marker group is present twice or once.

The linker used in the present invention may be a "linear" or a "branched" linker. Linear charged linkers are know from U.S. Pat. No. 5,958,783. Such a linear linker preferably has a chain length of 15-350 atoms and is an alkylene chain modified by the incorporation of heteroatoms such as amide functions. The linear linker containing the free charge carriers is preferably at least partially composed of aminocarboxylic acids units. Such aminocarboxylic acid units preferably are linked together via peptide bonds. The linker may contain naturally occurring as well as synthetic amino acid units. Preferably, the linker comprises repeatedly the dipeptide β-alanine-glutamic acid. A preferred linker structure comprises between 5 and 70 more preferred between 10 and 60 and most preferred between 15 and 50 times the dipeptide β-alanine-glutamic acid.

The linker in a further preferred embodiment is a branched linker.

The branched linker preferably contains a main chain which contains one or several uncharged hydrophilic groups, as mentioned above. In particular, the linker contains carboxylic acid amide groups or/and polyethylene glycol groups and further contains at least four charge carrying groups in one or several of the side chains. In this case, 1 to 10 charge carriers and in particular 1 to 5 charge carriers can for example be present per side chain.

Alternatively, the branched linker can also contain charge carriers in the main chain and uncharged hydrophilic groups in one or several of the side chains. Furthermore, embodiments are also conceivable in which the main chain and the side chains contain uncharged hydrophilic groups as well as charge carriers.

The branched linker has the additional advantage that it can be synthesized to carry several marker groups. Covalent coupling of such a linker (marker) structure brings about the introduction of several marker groups per biomolecule and per coupling event. Preferred linker (marker) structures carry two or four marker groups.

The length of the main chain of the branched linker is preferably 7 to 200 atoms, particularly preferably 7 to 100 atoms, in which case the main chain is an alkylene chain modified by the incorporation of heteroatoms e.g. O atoms or amide groups and contains at least one branch site, the side chains formed by the branching site preferably have a length of 4 to 100 atoms. The charge carriers are preferably located in the linker in such a manner that a H atom of an alkylene unit of the main chain or/and in a side chain is replaced by a group containing a charge carrier e.g. $NH_3^+$ or $CO_2^-$ or a guanidinyl group.

The branched linker, which contains the free charge carriers or/and hydrophilic groups, is preferably at least partially composed of aminocarboxylic acid units that are linked together by peptide bonds. In such a linker, the branching points can be derived from polyfunctional aminocarboxylic acids which contain at least three functional groups e.g. amino or carboxylate groups such that one functional group is still present after incorporation into the main chain which can be used as the starting point for the synthesis of the side chain. The branches are particularly preferably generated with diaminocarboxylic acids such as lysine, ornithine, hydroxylysine, α,β-diamino propionic acid etc.

The charge carriers of the branched linker can be preferably derived from free positively or/and negatively charged groups of polyfunctional amino-carboxylic acids, which contain a total of at least three charged groups (e.g. amino, carboxylate or phosphate groups) such that after incorporation into the linker and the concomitant reaction of two of the charged groups, at least one free charge carrier is still present. For example, the charge carriers can be derived from trifunctional aminocarboxylic acids which contain (a) an amino group and two carboxylate groups or (b) two amino groups and one carboxylate group. Examples of such trifunctional aminocarboxylic acids are lysine, ornithine, hydroxylysine, α,β-diamino propionic acid, arginine, aspartic acid and glutamic acid, carboxy glutamic acid and symmetric trifunctional carboxylic acids like those described in EP-A-0 618 192 or U.S. Pat. No. 5,519,142. Alternatively one of the carboxylate groups in the trifunctional aminocarboxylic acids (a) can be replaced by a phosphate, sulphonate or sulphate group. An example of such a trifunctional amino acid is phosphoserine.

Alternatively, the branched linker can also be composed, at least partially, of phosphate-sugar units e.g. a DNA backbone without nucleobases or composed of glyco-peptidic structures. Furthermore, the linker can also be composed, at least partially, of saccharide units. In any case, the side chain of the linker is preferably situated at a branch of the main chain, which is formed by a trifunctional unit and the length of a side chain is at least two of the building blocks used for the synthesis e.g. natural or synthetic amino acids or other components such as ethylene glycol.

According to the present invention, it is possible to couple a linker molecule having a molecular weight of 1 to 15 kD to a biomolecule of 5 to 500 kD and to isolate or select coupling products of uniform stoichiometry. The isolated fractions then optimally can be used to couple a second molecule to the first conjugate.

In a further preferred embodiment of a process according to the present invention, the charged linker molecule used in the chemical coupling to a biomolecule already carries one or several marker groups. Examples of marker groups are labeling groups and effector groups. At some places, the fact that the marker group may already be attached to the linker is additionally indicated by writing linker (marker).

Using the state of the art procedures, the smaller the marker group, the more difficult is the separation of conjugation products of uniform stoichiometry formed between a biomolecule and a marker.

Preferably, the marker group (labeling groups or effector groups) has a molecular weight below 15000 D, more preferred of less than 10000 D. Most preferred the marker group is even smaller than 5000 D. In a preferred embodiment the marker group attached to the linker has a molecular weight of 3000 D or less.

The complete molecular weight of such linker (marker), i.e. a linker together with the one or several marker groups preferably is 20 kD or less, more preferred 15 kD or less and most preferred 10 kD or less.

The labeling group can be selected from any detectable, known groups, such as dyes, luminescent labeling groups such as chemiluminescent groups e.g. acridinium esters or dioxetanes, or fluorescent dyes e.g. fluorescein, coumarin, rhodamine, oxazine, resorufin, cyanine and derivatives thereof. Other examples of labeling groups are luminescent metal complexes such as ruthenium or europium complexes, enzymes as used for CEDIA (Cloned Enzyme Donor Immunoassay, e.g. EP-A-0 061 888), and radioisotopes.

Effector groups comprise, for example, one partner of a bioaffine binding pair. While performing an assay, the effector group interacts specifically and preferably non-covalently with the other partner of the bioaffine binding pair. Examples of suitable binding partners include hapten or antigen and an antibody, biotin or biotin analogues (such as aminobiotin, iminobiotin or destheiobiotin) and avidin or streptavidin, sugar and lectin, nucleic acid or nucleic acid analogue and complementary nucleic acid, receptor and ligand e.g. steroid hormone receptor and steroid hormone. Preferably, the binding pair member of lower molecular weight is coupled to the linker before the linker (marker) is coupled to the biomolecule. Preferred molecular weight ranges as described for labeling groups also apply to the effector groups.

Preferred binding pair members include haptens, antigens, and hormones. Especially preferred are haptens, such as digoxin and biotin and analogues thereof.

Charged linear linker molecules—or linker structures already carrying a marker—are synthesized essentially as described in U.S. Pat. No. 5,958,783.

Branched charged linker molecules or linker (marker) molecules are e.g. obtained by solid phase synthesis. In a first step of the solid phase synthesis, an amino acid is coupled via its carboxylate group to the solid phase support and then the desired linker is synthesized by successively coupling further amino acids. In this process at least one amino acid which contains a charged group as a side group e.g. an amino group or a carboxylate group and at least one amino acid which serves as the branching site and is optionally in a protected form are used to prepare a linker according to the invention. After completion of the desired linker sequence the linker is either cleaved off the solid phase support or an activated marker, e.g. a marker carrying an active ester, can be coupled to the free N-terminal amino group of the peptide bound to the solid phase. After cleavage from the solid phase, a reactive group, Z, can be coupled to the carboxy terminus of the peptide linker or the carboxy terminus itself is used as a reactive group Z. Protecting groups that may be present are cleaved off.

In another mode of solid phase synthesis an amino acid marker conjugate which contains a protected amino group and a carboxylate group e.g. Fmoc-Lys(-Ru(bipyridyl)$_3$-OH) can be anchored to a solid phase by means of the free carboxylate group and a peptide linker can be synthesized after release of the blocked amino group. After completion of the desired linker sequence, the complex is cleaved from the solid phase. The reactive group Z can be coupled to the amino terminus of the resulting peptide linker, or the amino terminus itself is used to function as reactive group Z.

Chemical coupling of the biomolecule to a linker molecule leads to a statistical mixture of various biomolecule-linker products. In other words, such crude conjugates comprise a statistical mixture of many different coupling products, i.e., biomolecules which are not conjugated at all, biomolecules comprising one linker structure, biomolecules comprising two linker structures and so on. Each of these biomolecule-linker product subgroups is characterized by a uniform stoichiometry. This means that, e.g., the subgroup comprising one linker structure per biomolecule has a uniform stoichiometry of 1:1.

For example, hapten-protein-conjugates can be synthesized by incubating a chemically activated hapten with a protein in a predefined molar ratio. Specific coupling chemistries are known targeting different functional amino acid groups (—SH; —NH$_2$; —COO$^-$; —OH; imino groups of tyrosine, imidazole groups of histidine). Usually these groups are repeatedly present in the protein. As a consequence, the hapten will not be evenly distributed but rather the hapten will be bound to the protein in a Poisson distribution, which can be expressed as:

$$P(r)=m^r \times e^{-m}/r!$$

Where P(r) is the fraction of protein molecules with r (0, 1, 2, 3, etc.) haptens bound per molecules;
m is the average molar ratio between hapten and protein in the reaction mixture; e=Euler's number and r! represents faculty of r (e.g. in case of r=3, r!=3×2×1). This means for example, for a crude mixture of coupling products comprising on the average 1 hapten molecule bound per protein molecule, that statistically, roughly 36.7% of the protein molecules are not labeled at all, 36.7% carry one hapten molecule, 18.3% carry two hapten molecules, 6.1% carry three hapten molecules and the rest is even more highly labeled.

It is an extremely attractive feature of the present invention that now, for example, conjugates between a biomolecule and a small marker group (linked together by a linker molecule—where the linker molecule also has advantageous effects such as reducing background noise in immunolgical assays)—are now available in pre-determined and pre-defined amounts.

Conjugates known from the art are usually characterized by a labeling index. This labeling index indicates the average amount of labels (or linker (marker) groups) per biomolecule. A labeling index of 2.3 therefore signifies t that on average, 2.3 labels are present on each biomolecule. It is possible, by sophisticated methods, to determine the relative amounts of coupling products of uniform stoichiometry for example, using MALDI-TOF (matrix assisted laser desorption ionization-time of flight) mass-spectroscopy. However, such methods are not appropriate for separating fractions of uniform stoichiometry. The present invention allows for the production of a conjugate comprising at least one pre-selected biomolecule linker product of uniform stoichiometry in non-statistical amounts.

The term "pre-selected" is used to indicate that the inventive conjugate is not the mere statistical result of a chemical conjugation between a biomolecule and a linker molecule but rather that it is a result of pre-selection of appropriate fractions. One coupling product, or if required, several coupling products, of uniform stoichiometry can now be selected at will (as required) and the conjugate can be composed as appropriate for the intended application.

The mode and strategy of chemical coupling can be selected as required. In case the biomolecule is a polypeptide comprising —SH, —NH$_2$ or —COO$^-$ residues as functional groups, several appropriate coupling chemistries are known form the art for each of these functional groups and only some shall be mentioned. The careful reader will find all required details in Aslam, M. Dent, A. The preparation of protein-protein conjugates in "Bioconjugation" (1998) 216-363, London, McMillan.

Amino groups of biomolecules (the terminal —NH$_2$ group or the NH$_2$ group of a lysine side chain, as well as ω-amino groups of diamino carboxylic acids) can be used for chemical coupling of a marker group thereto based on "amino chemistry". Well-known examples of amino chemistry comprise amongst others the reaction of amino groups with so-called activated groups, like NHS-esters, other activated esters, acid chlorides and azides.

Carboxyl groups on biomolecules (the terminal COO$^-$-group, the carboxy functions of glutamic acid or aspartic acid) are used for chemical coupling based on "carboxy chemistry". Well-known examples of carboxy chemistry comprise, amongst others, the activation of these of carboxy groups to carry the above mentioned activated groups. Coupling to e.g., amino groups on the marker is then easily performed.

Alternatively, sulfhydryl groups on biomolecules (e.g. free-SH-groups of cysteine or —SH groups obtained by reducing di-sulfhydryl bridges) are used for chemical coupling based on "sulfhydryl chemistry". Well-known examples of sulfhydryl chemistry comprise amongst others the reaction of —SH groups with maleimido groups, or alkylation with α-halogen carboxylic group or thioethers.

The hydroxyl group of tyrosine residues or the imidazol group of histidine also may be used to covalent link markers to a biomolecule by aid, e.g., of diazonium groups.

The chemical reaction for coupling the biomolecule to the linker or the linker (marker) is performed as known from the art. Whereas in the art usually only the non-conjugated small linker or linker (marker) molecules are separated from the high molecular weight biomolecule-linker fraction, the separation of free biomolecule from conjugated biomolecule is very difficult or impossible. This separation and also the separation and selection of coupling products according to their stoichiometry is now possible and is performed by chromatographic procedures. The conjugation products are separated into fractions of uniform stoichiometry based on properties contributed by the linker structure.

Especially attractive properties of the novel biomolecule-linker products are differences in apparent molecular weight, hydrophobicity, and in charge. The differences for the various coupling products with different stoichiometry simply depend on the number of linker structures per biomolecule.

In a preferred embodiment the chromatographic fractionation is performed by a separation procedure based on (apparent) molecular weight. It was a very surprising finding that fractionation of the various coupling products with uniform but different stoichiometry is possible based on apparent molecular weight. Despite absolute differences in molecular weight that are comparatively small between coupling products of different stoichiometry, the differences in apparent molecular weight are quite pronounced. This is brought about by the linker molecules used in this invention. Although these molecules have a molecular weight of 1 to 15 kD, they migrate as having a very unusual and very high apparent molecular weight.

According to the invention, it now is possible to easily separate and if required, fractionate, e.g., Fab'-fragments of antibodies, which have a molecular weight of about 50 kD and carry one linker (label) molecule from Fab'-fragments carrying none, two, three, or more linker (label) molecules. This is exemplified in Examples 4 and 5 and in FIGS. 10 and 11. Such separation is possible, because the linker structures of the biomolecule-linker conjugates according to the present invention have been found to have apparent molecular weight which is much higher as their real molecular weight.

It is possible to separate the coupling products of uniform stoichiometry between even larger biomolecules, like e.g., F(ab')$_2$-fragments (about 100 kD), BSA or immoglobulin G and a linker or a linker (marker) molecule, once the larger biomolecule is coupled to an appropriate linker or a linker (marker).

The apparent molecular weight for a biomolecule can easily be determined according to procedures known in the art. Routinely used is, e.g., molecular sieve chromatography. The molecule of interest is chromatographed and the apparent molecular weight is determined by comparing the retention time for this molecule to the retention time or times of one or more molecular weight markers.

Since the apparent molecular weight is greatly influenced by the method used to determine it, the apparent molecular weight of the biomolecule and the apparent molecular weight of the linker or linker (marker) structure are determined by the same procedure.

For ease of separation by molecular weight chromatography, linkers are chosen which match the apparent molecular weight of the biomolecule. Preferably, the apparent molecular weight of the linker (marker) is at least 20% and at most 500% of the molecular weight of the biomolecule. A process for the production of a conjugate comprising at least one biomolecule-linker product of uniform stoichiometry in a pre-selected amount, said conjugate consisting of a biomolecule of a molecular weight between 5 kD and 500 kD and a hydrophilic linker molecule, said linker having a molecular weight between 1 kD and 15 kD, between 4 and 60 charged residues and an apparent molecular weight between 20% and 500% of the apparent molecular weight of said biomolecule, characterized in that a) the biomolecule and the linker molecule are covalent coupled to each other,
b) the different biomolecule-linker products of uniform stoichiometry are fractionated by chromatography based on the differences in apparent molecular weight of said biomolecule-linker products, and
c) fractions containing a coupling product of uniform stoichiometry are collected, therefore represents a preferred embodiment of the invention. More preferred the apparent molecular weight of the linker or the linker (marker) is between 25% and 400%, most preferred between 30% and 330% of the apparent molecular weight of the biomolecule.

Separation by (apparent) molecular weight preferably is performed by molecular sieve chromatography using chromatography materials like Sephadex S 200 HR®.

A further striking and characteristic feature of the linker structures used according to the present invention is the fact that they carry at least four charged residues per molecule. The high number of charged residues within the linker also leads to differences in net charge of the biomolecule-linker products; these charge differences being dependent on the number of linkers per biomolecule. E.g. based on differences in charge, biomolecule-linker products with one linker per biomolecule (of uniform 1:1 stoichiometry) can now surprisingly and easily be separated from biomolecule-linker products of different stoichiometry or from biomolecules without any linker attached.

In a preferred embodiment the invention relates to a process for the production of a conjugate comprising at least one biomolecule-linker product of uniform stoichiometry in a pre-selected amount, said conjugate consisting of a biomolecule of a molecular weight between 5 kD and 500 kD and a hydrophilic linker molecule, said linker having a molecular weight between 1 kD and 15 kD, between 4 and 60 charged residues, characterized in that a) the biomolecule and the linker molecule are covalent coupled to each other,
b) the different biomolecule-linker products of uniform stoichiometry are fractionated by chromatography, based on differences in charge of said biomolecule-linker products, and
c) fractions containing a coupling product of uniform stoichiometry are collected.

Preferably, standard chromatography materials and procedures, like ion exchange chromatography, e.g., employing Mono Q®, Mono S®, Source Q® or Source S® from Amersham-Pharmacia Biotech, are used to separate biomolecule-linker products of uniform stoichiometry based on charge differences. Fractions containing the desired products are collected. Individual biomolecule linker products of pre-selected stoichiometry or mixtures of several products of pre-selected stoichiometry and in pre-selected relative amounts are obtained. If desired, high purity levels are obtained by rechromatographing a fraction. Any desired, pre-selected ratio of conjugates can be obtained by pooling appropriate fractions.

As mentioned above, the coupling products of different stoichiometry also are different with respect to their hydrophilicity. The hydrophilic linker structures influence the overall hydrophilicity or hydrophobicity of the coupling products. Products of different stoichiometry in a preferred embodiment also are separated by hydrophobic interaction chromatography using state of the art resins, like Phenyl Sepharose HP®, Butyl Sepharose 4 Fast Flow® or others. Essential materials and procedures are described in Aslam, M. Dent, A. The preparation of protein-protein conjugates in "Bioconjugation" (1998) 216-363, London, McMillan. Reversed phase chromatography may also be used.

The conjugate produced according to the procedures described herein contains at least one uniform coupling product between a biomolecule and a linker molecule in the amounts desired. The relative amounts of each coupling product of uniform stoichiometry can be pre-selected as required. Pre-determined, desired relative amounts of individual coupling products of uniform stoichiometry can be exactly and reproducibly adjusted.

In a further preferred embodiment, the pre-selected conjugate is essentially free of non-conjugated biomolecules.

It is also preferred that based on the fractionation now possible, the inventive conjugate does not contain biomolecule-linker products in a stoichiometry of 1:5 and above.

In a preferred embodiment, the invention relates to a conjugate consisting of a biomolecule of a molecular weight between 5 kD and 500 kD and a hydrophilic linker molecule said linker having a molecular weight between 1 and 15 kD and between 4 and 60 charged residues, characterized in that said conjugate comprises at least one biomolecule-linker product of uniform stoichiometry in a pre-selected amount.

Any desired purity of individual coupling products of uniform stoichiometry can now be produced and reproduced. Mixtures containing various coupling products of uniform stoichiometry in ratios (relative amounts) as required can easily be produced and reproduced. The inventive conjugate therefore comprises at least one biomolecule-linker product of uniform stoichiometry in a pre-selected relative amount as compared to at least one other biomolecule-linker product of uniform stoichiometry.

The less biomolecule-linker products of uniform stoichiometry form part of the conjugate the more easy it is produced or reproduced. A preferred conjugate essentially comprises 1 to 3 individual biomolecule-linker products of uniform stoichiometry. Even more preferred the conjugate comprises essentially two different coupling products of uniform stoichiometry. In a most preferred embodiment the conjugate according to the present invention essentially comprises a biomolecule-linker product of 1:1 stoichiometry.

In a further preferred embodiment, the conjugate according to the present invention essentially comprises only one biomolecule-linker product of uniform stoichiometry.

Amongst the various coupling products, those with a uniform stoichiometry between 1:1 and 1:4 are preferred. Especially preferred are the biomolecule linker products with 1:2 and 1:1 stoichiometry, the latter representing the most preferred coupling product of uniform stoichiometry.

The term "essentially comprises" refers to the relative amount of one coupling product (or a mixture of up to three coupling products (each) of uniform stoichiometry as compared to the relative amount of other coupling products. In other words, at least 80% of all coupling products in such a conjugate are of the pre-selected stoichiometry. Preferably, "essentially comprises" relates to conjugates containing at least 80% of the uniform coupling product (or the desired mixture of coupling products). More preferred are conjugates comprising 90% of the pre-selected coupling-product or mixture of coupling products. Most preferred is a relative purity of 95% for the selected conjugate(s), as compared to the other coupling products.

In another preferred embodiment, the inventive conjugate comprises in a relative amount (as compared to other coupling products) at least 80% of two and most preferred at least 80% of only one biomolecule-linker product of uniform stoichiometry.

A very preferred conjugate comprises the coupling product of uniform 1:1 stoichiometry between a biomolecule with a molecular weight between 5 kD and 500 kD and a hydrophilic linker molecule said linker having a molecular weight between 1 and 15 kD and between 4 and 60 charged residues, in a relative purity of 80% or more. I.e. this 1:1 conjugate is present in a relative amount of 80% or above as compared to the sum of other biomolecule-linker products.

More preferred is a conjugate comprising the coupling product with 1:1 stoichiometry in a relative amount of 90% or above. Even more preferred are conjugates comprising the coupling product of 1:1 stoichiometry in a relative amount of 95% or above as compared to coupling products of different stoichiometry.

Nowadays, commercial assays are manufactured to require as little handling steps as possible. This is convenient and reduces the chances of handling errors. Of course, it is possible to provide the conjugate of the invention as such, e.g., frozen, or lyophilized to the customer.

It is preferred that the conjugate is part of a reagent composition. In many cases the conjugate is present in dilute and liquid form and therefore stabilizers, e.g. bovine serum albumin and/or various sugars are added and other reagents like preservatives and/or detergents are optionally present. In a further preferred embodiment, the invention relates to a composition of reagents comprising buffer components, a stabilizing reagent and a conjugate containing at least one biomolecule-linker product of uniform stoichiometry in a pre-selected amount.

Preferably the conjugate as produced according to the present invention is used in a test strip type immunological device.

Usually, not a single reagent but rather complete kits, containing at least the analyte-specific assay reagents are provided to the customer. In a preferred embodiment, the invention relates to a test kit for biochemical or immunological detection of an analyte in a sample, said kit comprising appropriate buffers and reagents and at least one composition of reagents comprising a conjugate according to the present invention.

Immunoassays based on the novel conjugates have superior characteristics, as compared to assays based on conjugates produced with methods in the art. This positive effect on the assay itself is shown in the Examples section. Strikingly, the background problem is significantly reduced if the novel conjugate is used under otherwise comparable assay conditions. The use of a conjugate comprising a member of a specific binding pair as described in the present invention in an immunoassay therefore represents another preferred embodiment of the invention.

Preferably, the novel conjugate is used in the detection of an analyte, where the detection is based on the reaction between an analyte specific binding partner and the analyte and measuring the resulting analyte binding partner complex. Best known examples of specific binding assays are immunoassays. In immunoassays based on a biomolecule-linker (marker) conjugate, the novel processes and reagents contribute to the reproducible preparation of the conjugates. The more reproducibly the conjugates are prepared, the more reproducible are the assays based thereon.

As discussed, the state of the art provides, to a limited extent, procedures capable of influencing both the quality of the conjugates as well as their reproducible production. While using state of the art methods, it is possible to remove aggregates or precipitates from the final conjugate, it is not possible to adjust the relative amounts of the coupling products of different stoichiometries between the biomolecule and the linker molecule. Using state of the art methods, it is very difficult if not impossible to select the fraction(s) containing those coupling product(s) of uniform stoichiometry which is (are) best suited for the intended application. These disadvantages have been overcome with the present invention.

The following examples, references, and figures are provided to aid the understanding of the present invention; the true scope of which is set forth in the appended claims. It is understood that modifications can be made in the procedures set forth without departing from the spirit of the invention.

LEGEND TO THE FIGURES

FIG. 1: Schematic representation of coupling BSA and the hy-BPRu-linker

The schematic for BSA illustrates the fact that several —$NH_2$ groups are available for binding to the by BPRu-linker (marker).

FIG. 2: Superdex 200 HR® chromatograph of a BSA-hy-BPRu-conjugate

This chromatograph demonstrates that the coupling products with different stoichiometries migrate as a single uniform peak. This single peak represents a statistical mixture of coupling products.

FIG. 3: Schematic of BPRu-(UE)$_{25}$ K and BPRu-(UE)$_{50}$ K

These linker structures repeatedly contain the di-peptide β-alanine-glutamic acid (UE).

FIG. 4: Branched linker with short backbone chain

This branched linker contains charged residues both in the short backbone, as well as in the side chains.

FIG. 5: Branched linker with long backbone chain

This branched linker contains charged residues in both the long backbone, and in the side chains.

FIG. 6: Branched linker without charged residues

This linker is very similar to the linker of FIG. 4 but does not carry charged residues of glutamic acid, instead glutamine is used. The apparent molecular weight has been found to be about 3.5 kD as compared to 18 kD for the linker of FIG. 4.

FIG. 7: Schematic of biotinylated linker molecules

These N-terminally biotinylated (Bi-) linker molecules carry at the C-terminus -MH and -DSS groups respectively, which are used for coupling to a biomolecule.

FIG. 8: Multiply branched linker

This schematic depicts a multiply branched linker with branched side chains, carrying two ruthenium labels (BPRu).

FIG. 9: Superdex 200 HR® chromatography of various linker molecules

BSA and the different linker molecules have been chromatographed under identical conditions. The upper panel shows linker structures according to FIGS. 4 and 6. The lower panel shows linker structures according to FIG. 3.

FIG. 10: Mono Q® chromatograph of a crude BSA-Ru (SK)$_4$-MH conjugate

The chromatograph shows baseline separation of BSA (1) and conjugation products of uniform 1:1 (2) and 1:2 (3) stoichiometry, respectively.

FIG. 11: Source 15 Q® chromatograph of a crude BSA-Ru(UE)$_{25}$-MH conjugate

Three conjugates of uniform stoichiometry 1:1; 1:2 and 1:3 (2, 3 and 4, respectively) are clearly separated from one another, as well as from non-conjugated BSA (1).

FIG. 12: Superdex 200 HR® chromatograph of a first Fab'-Ru(UE)$_{25}$-MH coupling product The crude conjugate is separated into three major peaks. Peak III which migrates with an apparent molecular weight of 50 kD comprises both the non-reacted Fab' as well as non-reacted linker (Ru-(UE)$_{25}$-MH). Peak II, which migrates with an apparent molecular weight of 100 kD comprises in essentially pure form, the 1:1 coupling product between Fab' and linker (marker). Peak I comprises the 1:2 coupling product (apparent molecular weight of 150 kD). Compositions of each pool has been confirmed by MALDI-TOF MS.

FIG. 13: Superdex 200 HR® chromatograph of a second Fab'-Ru(UE)$_{25}$ coupling product.

Peaks 1, 2 and 3 correspond to fractions containing conjugates of 1:3, 1:2 and 1:1 stoichiometry, respectively. Peaks 4 and 5 contain the un-conjugated starting materials (linker and Fab'-fragments). All structures have been confirmed by MALDI-TOF-MS.

FIG. 14: Purification of F(ab')$_2$-BPRu-(UE)$_{25}$-DSS coupling products

Crude conjugate is separated by Superdex 200 HR® chromatography. The peaks containing the 1:2 and the 1:1 coupling products are pooled separately and re-chromatographed. The composition of these coupling products has been confirmed by MALDI-TOF-MS.

FIG. 15: Purification of F(ab')$_2$-BPRu-UEEK-DSS coupling products

Crude conjugate is separated by Superdex 200 HR® chromatography. Only one symmetric "product peak" is found, comprising a statistical mixture of coupling products with different stoichiometries.

FIG. 16: Purification of IgG-(Bi-(UE)$_{25}$-DSS coupling products

Crude conjugate is separated by Source 30® chromatography. Non-conjugated IgG (pool 1) is easily eluted from the column. Mono-biotinylated IgG is pooled (pool 2) and clearly separated from the di-biotinylated IgG (pool 3).

EXAMPLE 1

Ruthenylation of Bovine Serum Albumine According to the State of the Art

Bovine serum albumine and a linker known in the art (see FIG. 1) have been used to set up 5 conjugation mixtures. All variables like lot-size, concentrations of reagents, buffer compositions, time of reaction, temperature of reagents as well as chromatographic separation procedures have been kept constant.

BSA was dissolved in a 100 mM potassium phosphate buffer (pH 8.0) at a concentration of 20 mg/ml. The hy-BPRu linker (label; cf. FIG. 1, top) was dissolved in DMSO at a concentration of 47 mg/ml. A 5-fold molar excess of hy-PBRu was added to the BSA solution, the reagents thoroughly mixed and reaction performed for 75 min at 25° C. The reaction was stopped by addition of lysine to a final concentration of 10 mM and incubated with stirring for an additional 30 min at 25° C.

Free non-bound derivatization reagents were completely removed by dialysis (20 hours at 4° C.) against phosphate buffered saline with 50 mM phosphate 150 mM sodium chloride at pH 7.5 (PBS), which has been used in 500-fold excess.

The active groups (the O-hydroxysuccinimide ester in FIG. 1) react statistically with the different $NH_2$-groups of BSA. The resulting crude conjugate has been chromatographed by Superdex 200 HR® chromatography using buffer conditions of 0.05 mmol/l sodium phosphate, 0.05 mmol/l sodium chloride and 5% methanol at pH 6.5. Elution is monitored. Appropriate fractions are pooled. The product peak was analyzed by electrospray-ionization mass-spectroscopy (ESI-MS). The results of such analysis are summarized in Tables 1 and 2.

using a Superdex 200 HR® column, all reaction products elute as a homogeneous peak. Fractionation of coupling products e.g., into a fraction containing uniformly a 1:1 conjugate, is not possible.)

EXAMPLE 2

Synthesis of Linker Structures

Synthesis of Branched Linker Structures
Preparation of Branched Linkers by Means of Solid Phase Peptide Synthesis The branched linkers were synthesized by means of fluorenylmethyloxycarbonyl-(Fmoc)-solid phase peptide synthesis on a batch peptide synthesizer e.g. from Applied Biosystems A433. In each case 4.0 equivalents of the amino acid derivative shown in table 3 were used.

TABLE 1

Distribution of BSA-Ruthenium conjugates according to molecular weight

| Lot | Labeling index RSA: BPRu | Stoichiometry 1:0 | Stoichiometry 1:1 | Stoichiometry 1:2 | Stoichiometry 1:3 | Stoichiometry 1:4 |
|---|---|---|---|---|---|---|
| BSA unmodified | 0 | 66500 D | | | | |
| Conjugate Ch1 | 1:2.3 | | 68300 D | 69400 D | 70400 D | 71300 D |
| Conjugate Ch2 | 1:2.3 | 66500 D | 68300 D | 69500 D | 70500 D | |
| Conjugate Ch3 | 1:2.8 | | 68500 D | 69600 D | 70700 D | 71800 D |
| Conjugate Ch4 | 1:2.9 | | 68000 D | 69200 D | 70300 D | |
| Conjugate Ch5 | 1:3.1 | | | 69400 D | 70600 D | 71500 D |

TABLE 2

Relative amounts of the different coupling products
(the most abundant coupling product has been set to 1 and
the others are expressed as relative amounts thereto).

| Lot | Labeling index RSA: BPRu | Stoichiometry 1:0 | Stoichiometry 1:1 | Stoichiometry 1:2 | Stoichiometry 1:3 | Stoichiometry 1:4 |
|---|---|---|---|---|---|---|
| BSA unmodified | 0 | 1.00 | | | | |
| Conjugate Ch1 | 1:2.3 | | 0.77 | 1.00 | 0.57 | 0.40 |
| Conjugate Ch2 | 1:2.3 | 0.48 | 0.48 | 1.00 | 0.71 | |
| Conjugate Ch3 | 1:2.8 | | 0.38 | 0.78 | 1.00 | 0.62 |
| Conjugate Ch4 | 1:2.9 | | 0.59 | 1.00 | 0.57 | |
| Conjugate Ch5 | 1:3.1 | | | 0.54 | 1.00 | 0.56 |

It is obvious from tables 1 and 2 that all 5 lots, though produced under identical conditions clearly are different from one another. Lot 1 and 2 have the same overall labeling index of 2.3 (this means in the average 2.3 ruthenium labels are found per BSA molecule). Nonetheless, both preparations differ significantly in the relative amounts of the individual conjugation products as is evident from Table 2. Also the overall labeling indices vary quite significantly. It is evident from FIG. 2 that by standard chromatographic procedures

TABLE 3

| A | Fmoc-Ala-OH |
|---|---|
| C | Fmoc-Cys(Trt)-OH |
| D | Fmoc-Asp(OtBu)-OH |
| E | Fmoc-Glu(OtBu)-OH |
| gE | Fmoc-Glu-OtBu |
| F | Fmoc-Phe-OH |
| G | Fmoc-Gly-OH |
| H | Fmoc-His(Trt)-OH |

TABLE 3-continued

| | |
|---|---|
| I | Fmoc-Ile-OH |
| K1 | Fmoc-Lys(Boc)-OH |
| K2 | Fmoc-Lys(Fmoc)-OH |
| K3 | Fmoc-Lys(Dde)-OH |
| K4 | Fmoc-Lys(Alloc)-OH |
| K5 | Fmoc-Lys(PhAc)-OH |
| K6 | Fmoc-Lys-(label)-OH |
| K7 | Boc-Lys(Fmoc)-OH |
| L | Fmoc-Leu-OH |
| M | Fmoc-Met-OH |
| N | Fmoc-Asn(Trt)-OH |
| P | Fmoc-Pro-OH |
| Q | Fmoc-Gln(Trt)-OH |
| R | Fmoc-Arg(Pmc)-OH |
| S | Fmoc-Ser(tBu)-OH |
| T | Fmoc-Thr(tBU)-OH |
| U | Fmoc-β-alanine-OH |
| V | Fmoc-Val-OH |
| W | Fmoc-Trp-OH |
| Y | Fmoc-Tyr(tBU)-OH |
| Z | Fmoc-ε-amino caproic acid |
| Ps | Fmoc-Ser(PO(OBzl)OH)-OH |
| Cs | Fmoc-Cys(SO3H)-OH |

The amino acids and amino acid derivatives were dissolved in N-methyl-pyrrolidinone. The peptide is synthesized on Wang resin (S.-S. Wang, J. Am. Chem. Soc. 95 (1973) 1328). The resin is loaded with 0.2 to 0.4 mMol/g. The coupling reactions were carried out for 20 minutes using 4 equivalents dicyclohexylcarbodiimide and 4 equivalents N-hydroxybenzotriazole in dimethylformamide relative to the Fmoc-amino acid derivative in dimethylformamide as the reaction medium. The Fmoc group was cleaved after each step of the synthesis with 20% piperidine in dimethylformamide for 20 min. The amount of resin was selected such that after the last branch, 4 equivalents Fmoc-amino acid relative to the amino groups are used. Fmoc-Lys(Fmoc)-OH is used for the branch and subsequent synthesis of two identical arms. Non-symmetric branches are achieved by amino acid derivatives with orthogonal side chain protective groups such as Fmoc-Lys (Dde) or Fmoc-Lys(Alloc). These orthogonal protective groups are cleaved on the resin by methods known in the literature (B. W. Bycroft et al. (1993), J. Chem. Soc., Chem. Commun., 778; A. Merzouk et al., (1992) Tetrahedron Lett. 33, 477). Terminal amino groups on the solid phase are optionally acetylated or succinylated with acetic anhydride or succinic anhydride.

The hapten, label or functional group in those cases where the derivative is stable during the solid phase synthesis was already introduced on the resin e.g. on the N-terminal amino acid of the peptide.

The introduction of e.g. a metal chelate label was carried out via appropriate active ester derivatives at the free N-terminal amino group of the carrier-bound peptide. For this four equivalents ruthenium(bipyridyl)3 complex (BPRu) per free primary amino function were activated with N-hydroxybenzotriazole/dicyclohexyl-carbodiimide and dissolved in a small amount of DMSO and this was added drop-wise and stirred for 2 h at room temperature.

The marker can also be introduced at the C-terminus already during the solid phase synthesis by the direct incorporation of, for example, a metal chelate or biotin-coupled amino acid derivatives (described in WO 96/03409).

The peptide is released from the support and the acid-labile protective groups are cleaved with 20 ml trifluoroacetic acid, 0.5 ml ethanediol, 1 ml thioanisole, 1.5 g phenol and 1 ml water for 40 min at room temperature. Depending on the amino acid derivatives that are used, it is also possible to use cocktails containing fewer radical traps. 300 ml cooled diisopropyl ether was subsequently added to the reaction solution and the mixture was kept for 40 min at 0° C. in order to completely precipitate the peptide. The precipitate was filtered, washed with diisopropyl ether and dissolved in a small amount of 50% acetic acid and lyophilized. The crude material obtained was purified by means of preparative HPLC on Delta-PAK RP C18 (column 50×300 mm, 100 Å; 15µ over an appropriate gradient (eluant A: water, 0.1% trifluoroacetic acid, eluant B: acetonitrile, 0.1% trifluoroacetic acid) within ca. 120 min. The eluted material was identified by mass spectrometry.

Alternatively, the marker group can also be introduced after cleavage from the resin. For this it may be necessary to block other groups that should not be derivatized with a protective group, which is stable during the solid phase peptide synthesis as well as during the cleavage. E.g. phenylacetyl (Phac) may be used and the protective group removed enzymatically with PenG amidase (described in PCT/EP 95/02921).

b) Synthesis of Linear Charged Linker Structures

Linear charged linker structures have been synthesized essentially as described in U.S. Pat. No. 5,958,783.

c) Examples of Linker Structures Investigated.

Table 4 gives an overview over some of the linker structures used. Structure 1 and 10 are structures know from the art, whereas all other structures comprise additional features, e.g., a strikingly high apparent molecular weight.

Where available, laboratory names have also been given. References are made to the Figures in which these structures (or basic structures used for MH- or DSS-activation) are given.

TABLE 4

Overview of linker structures (linear or branched)

| No. | Lab-name | Fig | MW [D] | MW (a) |
|---|---|---|---|---|
| 1 | hy-BPRu | 1 | 1773 | ~2 kD |
| 2 | BPRu(UE)$_{25}$ K | 3 | 5802 | ~50 kD |
| 3 | BPRu(UE)$_{50}$ K | 3 | 10807 | ~70 kD |
| 4 | BPRu(UE)$_{25}$-K-MH | [3] | 5996 | ~50 kD |
| 5 | BPRu(UE)$_{25}$-K-DSS | [3] | 6056 | ~50 kD |
| 6 | BPRu(UE)$_{50}$-K-MH | [3] | 11001 | ~70 kD |
| 7 | BPRu-SK(2) charged | 4 | 3004 | ~18 kD |
| 8 | BPRu(UE)$_{25}$-K-MH branched | 5 | 8010 | ~70 kD |
| 9 | BPRu(UE)$_{25}$-K-DSS branched | 5 | 8072 | ~70 kD |
| 10 | BPRu-SK(2) not charged | 6 | 3392 | 3.5 kD |
| 11 | BPRu(UE)$_{25}$-K-MH | [7] | 5570 | ~50 kD |
| 12 | BPRu(UE)$_{25}$-K-DSS | [7] | 5630 | ~50 kD |
| 13 | BPRu(SK)$_4$-DSS multiply branched linker | 8 | 6457 | ~60 kD |

(a) Apparent molecular weight
n.d. not determined
n.s. not shown
MH maleimide activated
DSS N-hydroxysuccinimidylsuberate
Bi biotin
[ ] basic structure shown in Figure [ ]

FIG. 9 shows Superdex 200 HR® chromatographs of linker (marker) structures in comparison to BSA. The dramatic influence of charged residues becomes evident from the top panel, whereas the uncharged linker migrates with a molecular weight of about 3 500 D the charged linker is found with an apparent molecular weight of about 18 000 D. FIG. 9 bottom panel demonstrates the great effects which a long charged backbone of a linker molecule has on differences in apparent molecular weight. Structure 2 (BPRu-(UE)$_{25}$) which has a molecular weight of 5,802 for example migrates with an apparent molecular weight of around 50,000 D.

As already indicated in table 4, the linker molecules may be activated. An example for activation is the introduction of a maleinimido function. In order to introduce the maleinimide function, a linker e.g. produced according to example 2, is dissolved in 0.1 M potassium phosphate buffer (pH 7.0) and mixed with one equivalent maleinimidohexanoic acid N-hydroxysuccinimide ester (dissolved in DMSO) and stirred for 16 h at 25° C. The preparation is purified by preparative HPLC using an RPC18 column (see above). The identity of the eluted material is checked by means of mass spectrometry.)

EXAMPLE 3

Novel Bovine Albumine Linker Conjugates

As described in WO 96/03652, carrier molecules comprising multimeric antigens are of great advantage in the detection of anti-viral-antibodies. For production of a polyhapten, the amino groups of carrier molecule first are activated using a active ester group. This active ester group is selected to match the corresponding active group on the marker group used. Preferred active groups are the maleinimidohexyl (MHS) or maleinimidopropyl-N-hydroxysuccinimide ester (MPS). As a result primary amino groups in the carrier (for example the $\epsilon$-amino side chains of lysine residues) partially are derivatized to carry the desired maleinimido groups. After coupling the marker group to the activated carrier the —$NH_2$ groups of the carrier are present either unmodified, or carrying an MHS group, or carrying a label via the MHS-linker.

The linker (marker) structures schematically shown in FIGS. 3 (DSS-activated) and 8 have been coupled to BSA under identical conditions.

BSA is dissolved in 0.1 mmol/l potassium phosphate buffer of pH 7.5 in a concentration of 10 mg/ml. The linker (marker) is added in a molar ratio of 4.5 per mole of BSA. Reaction is performed for 3 hours at room temperature. The reaction product is subjected to ion exchange chromatography. Separation of coupling products with uniform stoichiometry is achieved by using a Source 15 Q® or a Mono Q® column.

The crude conjugate of the multiply branched linker (cf. FIG. 8 and structure 13 of table 1) was fractionated with Mono Q® chromatography. Elution was performed using a salt gradient from 20 mM potassium phosphate buffer (pH 6.5) (=eluent A) to 1M sodium chloride in 20 mM potassium phosphate buffer (pH 6.5) (=eluent B). Elution is monitored at 280 nm. The gradient shown in FIG. 10 covers the range of 25 to 54% eluent B and corresponds to 30 min of elution. Appropriate fractions are pooled. Fractions are analyzed by MALDI-TOF-MS. MS data confirmed that each of the three peaks contained in pure form BSA (1 in FIG. 10) and BSA molecules carrying 1, or 2 linker (marker) groups (2, and 3 in FIG. 10, respectively).

The crude conjugate obtained with the long and strongly negatively charged linear linker (cf. structure 12 from table 4 and FIG. 3) has been separated by Source 15 Q® chromatography. Elution was performed using a salt gradient from 20 mM potassium phosphate buffer (pH 6.5) (=eluent A) to 1M sodium chloride in 20 mM potassium phosphate buffer (pH 6.5) (=eluent B). Elution is monitored at 280 nm. The gradient shown in FIG. 10 covers the range of 30 to 40% eluent B and corresponds to 30 min of elution. Appropriate fractions are pooled. Fractions are analyzed by MALDI-TOF-MS. MS data confirmed that each of the four peaks contained in pure form BSA (1 in FIG. 11) and BSA molecules carrying 1, 2 or 3 linker (marker) groups (2, 3 and 4 in FIG. 11, respectively).

EXAMPLE 4

Production of a First Novel Fab'-Linker-Conjugate

1. Description of the Procedure
    1.1. Preparation of the Fab' from IgG
    A monoclonal antibody to digoxin (anti-Dig) was cleaved by pepsin to form F(ab')$_2$. After quantitative cleavage, the pepsin was inactivated by increasing the pH and adding pepstatin. The F(ab')$_2$ was reduced by means of cysteamine to Fab' without prior purification. Cysteamine cleaves almost selectively the disulfide bridges in the hinge region. It was subsequently dialysed. This removes most of the Fc cleavage products generated by pepsin since they are small enough to pass through the pores of the dialysis tube, which has a cutoff of 10,000 Dalton.
Fab'-BPRU Linker Conjugate
    The conjugate synthesis was carried out via —SH group chemistry by reacting the Fab' with an excess of BPRu-linker-MH. In this process an SH group in the hinge region was mainly converted. Small amounts of polyruthenylated Fab' were formed as a side reaction as a result of reduced intramolecular disulphide bridges in the light and in the Fd chain.
    1.2. Purification of the Crude Conjugate
    The crude conjugate was purified using molecular sieve chromatography. In this process the mono-ruthenylated material was separated from the poly-ruthenylated material.
2. Procedure
    2.1. Cleavage of the Antibody to Form F(ab')$_2$
    The lyophilisate of the monoclonal antibody anti-DIG-M19.11 IgG was reconstituted with H$_2$O to obtain a concentration of 20 mg/ml. 20 μl 1 M citrate pH 3.5 were added per ml solution (final concentration citrate=20 mM). The pH was adjusted with HCl to 3.60. It was filtered through a 0.45 μm filter. The concentration was determined at OD 280 nm (1 OD280 nm=1.4 mg/ml). It was adjusted to 10 mg/ml with 20 mM citrate pH 3.60. The solution was heated in a water bath to 37° C. 100 μl pepsin solution (3 mg/ml) was added per ml antibody solution and incubated at 37° C. in a water bath. After complete cleavage, the reaction was stopped by increasing the pH value and adding pepstatin.
    2.2. Reduction to Fab'
    52.6 μl 0.1 M dithiothreitol (DTT) was added per ml of cleavage mixture and incubated for 30 min at 25° C. in a water bath. The Fab' was dialyzed against 0.1 M NaH$_2$PO$_4$/NaOH pH 6.5, 30 mM NaCl, 2 mM EDTA.
    2.3. Synthesis of the Fab'-BPRu-Linker Conjugate
    The BPRu-linker-MH (the branched linker of FIG. 8, but carrying a DSS instead of an MH group) was dissolved in DMSO. The stoichiometry Fab':BPRu-linker-MH was 1:3 (mole/mole). The final concentration of Fab' in the mixture was 3.9 mg/ml. The maximum concentration of DMSO in the mixture was 10%. The reaction time was 1 h at room temperature.
    2.4. Purification
    The crude conjugate was concentrated 2-3-fold using an Amicon PM 10 and purified by means of Superdex 200 HR® (buffer: 25 mM MOPS/NaOH pH 6.5, 50 mM NaCl, 10% DMSO; applied amount: max 1.5% of the gel bed, fractions: 0.5% of the gel bed). The fractions containing the Fab'-BPRu-linker conjugate were pooled. If required, re-chromatography can be performed.
    The crude conjugate predominantly contains coupling products consisting of Fab'-fragments to which at one of the —SH-groups in the hinge region a linker is bound. To a smaller extent also multiply labeled Fab'-fragments are also present (cf. peaks III, II, and I, respectively, in FIG. 12).

EXAMPLE 5

Production of a Second Novel Fab'-BPRu(UE)$_{25}$-Conjugate

1. F(ab')$_2$ and Fab'-Fragments were Prepared from an Anti-HIV p24 Monoclonal

Fragmentation is essentially performed as described in Example 4. The F(ab')$_2$-solution is dialyzed against 50 mM potassium phosphate, and 150 mM sodium chloride buffer at a pH of 7.5. To an F(ab')$_2$-solution containing 5 mg/ml F(ab')$_2$-fragments, cysteamine in a final concentration of 25 mM is added. The solution is incubated for 60 minutes at 37° C. Reaction is stopped via buffer change using a PD10-column buffer to pH 6.0 with a 50 mM sodium phosphate, 150 mM sodium chloride buffer.

2. Ruthenylation of Fab'-Fragment

The linker BPRu-(UE)$_{25}$-MH is dissolved in DMSO in a concentration of 25 mg/ml. The molar ratio of Fab'-fragments to BPRu-(UE)$_{25}$-MH linker (maker) is set at 1 to 2. The reaction mixture is incubated for 90 minutes at 25° C. in a 50 mM potassium phosphate, and 150 mM sodium chloride solution (pH 7.1). The reaction is stopped by addition of 2 mM cysteine and incubation of the solution for 30 minutes at 25° C. N-methyl-maleinimid is added at 5 mM and incubated for 60 minutes at 55° C.

3. Purification

The crude conjugate was concentrated about 3-fold using a CENTRICON 10 and purified by means of a Superdex 200 HR® column buffered to pH 7.5 with 50 mM potassium phosphate, and 150 mM sodium chloride. As can be seen from FIG. 11, the crude mixture has been found to contain non-conjugated Fab'-fragment, non-conjugated linker (marker) as well as conjugates of uniform stoichiometries of 1:1, 1:2 and 1:3 (cf. peaks 5 and 4, 3, 2, and 1, respectively of FIG. 13).

EXAMPLE 6

Ruthenylation of F(ab')$_2$-Fragments

1. Description of the Procedure 1.1. Production of F(ab')$_2$ Fragments of IgG

The same monoclonal antibody as known from Example 5 is used for production of F(ab')$_2$-fragments. Digestion of IgG by pepsin is performed as described in Example 5. After quantitative cleavage pepsin is inactivated by increasing the pH and by adding pepstatin. F(ab')$_2$-fragments are purified using Superdex 200 HR® column chromatography.

1.2. Synthesis of F(ab')$_2$-BPRu-(UE)$_{25}$-DSS

Conjugation is performed by coupling the active group of BPRu-(UE)$_{25}$-DSS (the linker of FIG. 3 carrying a DSS group) to amino groups of the F(ab')$_2$-fragment. Dependent on the initial concentration of reagents as well as to the stoichiometry chosen between the F(ab')$_2$-fragments and the linker (marker) molecules, a crude conjugate is obtained with a higher or lower average labeling index. In other words, a random Poisson distribution of Fab'-molecules is obtained which carry varying amounts of linker structures.

1.3. Purification of Crude Conjugates

The crude conjugate is concentrated and purified using routine molecular sieve chromatography.

Due to the unusually high apparent molecular weight, as contributed to by each individual linker molecule, the coupling products of different stoichiometries can be separated from one another.

2. Procedure 2.1. Cleavage of IgG to F(ab')$_2$

Cleavage of Mab<p24>M-6D9-IgG to Mab<p24>M-6D9-F(ab')$_2$. Lyophylised IgG of a monoclonal antibody against p24 of HIV is reconstituted with H$_2$O to a final concentration 20 mg/ml. Cleavage is performed as described in Example 5.

2.2. Purification of F(ab')$_2$-Fragments by Superdex 200 HR® Chromatography.

The F(ab')$_2$-fragment produced as described are purified using the following buffers and conditions:

| | |
|---|---|
| Column material | Superdex 200 HR ® |
| Buffer | 10 mM sodium phosphate, buffer adjusted to pH 7.5 30 mM sodium chloride |
| Fluoride | 10 ml/cm$^2$/h |
| Sample volume | 1.5% of that volume of the column |
| Concentration of sample | 20 mg/ml |
| Monitoring of eluate photometer | 280 nm |

The fractions containing F(ab')$_2$-fragments are pooled concentrated and re-chromatographed under identical conditions.

2.3. Labeling of F(ab')$_2$-Fragments with BPRu-(UE)$_{25}$-DSS

BPRu-(UE)$_{25}$-DSS is dissolved in DMSO at 5 mg/ml. Coupling stoichiometry is chosen at 1:5 (mol/mol)=F(ab')$_2$-fragments:linker The reaction mixture is incubated for 1 h at room temperature. Reaction is stopped by addition of lysine to a final concentration of 10 mM.

2.4. Coupling of F(ab')$_2$-Fragments with BPRu-UEEK-DSS

The linker (label) BPRu-UEEK-DSS is dissolved in DMSO at a concentration of 5 mg/ml. The stoichiometry chosen for coupling is
1:5 (mol/mol)=F(ab')$_2$-fragments:BPRu-UEEK-DSS.

The reaction mixture is incubated for 1 h at room temperature. Reaction is stopped by addition of lysine to a final concentration of 10 mM.

2.5. Purification of Crude Coupling Products

Purification is performed by Superdex 200 HR® chromatography. Chromatography of both F(ab')$_2$-conjugates is performed in a 100 mM Hepes-buffer adjusted to pH 7.5, containing 1 mM EDTA and 5% DMSO. The flow rate is set to 5 ml/cm$^2$/h. Detection is performed at 280 nm. Sample volume is 1.5% of column volume.

As it is obvious from FIGS. 14 and 15 only the coupling products produced with the strongly negatively charged linker hy-BPRu-(UE)$_{25}$-DSS (FIG. 14) can be separated into fractions containing coupling products of uniform stoichiometry, whereas all coupling products using the conventional linker (FIG. 15) elute as one peak. The pooled fraction containing the majority of coupling products with 1:1 stoichiometry (ca. 107 min to 125 min; peak at 111 min in FIG. 14) has been re-chromatographed once and purity as well as molecular weight been confirmed by MALDI-TOF MS.

EXAMPLE 7

Immunoassay Using Different Antibody-Linker Conjugates

A double-antigen-test which is used for example in the detection of specific antibodies against HIV has been used as a model system. The sample (suspected to contain antibodies against HIV) is incubated with a biotinylated antigen and a digoxigenin-labeled antigen in the presence of a streptavidin-coated solid phase and an BPRu-labeled antibody against digoxin. In the presence of anti-HIV-antibodies in a sample a detection complex is formed comprising the streptavidin-coated solid phase the biotinylated antigen the antibody to be detected, the digoxinylated antigen and the ruthenium-labeled antibody reactive with digoxin. The detection of anti-HIV-antibodies is performed by measuring the electrochemiluminescence-signal bound to the solid phase according to standard electrochemiluminescence procedures.

In this model system, an N-terminally labeled HIV peptide from the gp41-region of HIV 1 has been used. Details relating to this peptide and to the labeling of this peptide are described in WO 96/03423. Both antigens have been used in a concentration of 20 ng/ml.

All components of the system have been kept constant and only the detection system, i.e., the ruthenium-labeled anti-digoxin reagent has been varied. For all conjugates listed in Tables 5 and 6 a Fab'-fragment of an anti-DIG antibody has been used at the same concentration of ruthenium label.

TABLE 5

Absolute counts measured

| experiment [counts] | conjugate E | conjugate F | conjugate G | conjugate H |
|---|---|---|---|---|
| negative sample | 488 | 895 | 394 | 282 |
| Positive sample 1 | 65108 | 74993 | 59379 | 68469 |
| Positive sample 2 | 119557 | 138898 | 113507 | 134360 |

TABLE 6

Reaction normalized to negative sample

| experiment pos./neg. sera | conjugate E | conjugate F | conjugate G | conjugate H |
|---|---|---|---|---|
| negative sample | 1.0 | 1.0 | 1.0 | 1.0 |
| positive sample 1 | 133.4 | 83.8 | 150.7 | 242.8 |
| positive sample 2 | 245.0 | 155.2 | 288.1 | 476.5 |

Conjugates E and F have been produced according to EP 720 614 using molar ratios of 1:2 and 1:6 (Fab' to linker), respectively. The linker used was KEEU-BPRu.

Conjugates G and H contained the purified 1:1 coupling products produced and purified according to the present invention comprising the linker (label) structures shown in FIGS. 3 ((UE)$_{25}$ and MH-activated) and 4, respectively.

The novel 1:1 conjugate allow for a better separation of positive sample from negative samples. This is most easily seen from table 6 where the signals obtained for the positive sere are normalized to the negative serum.

EXAMPLE 8

Conjugation of Monoclonal Antibody (MAB)<Ferritin>M-4.184 to a Biotinylated Linker (Bi-(UE)$_{25}$-DSS)

In this example, a complete MAB of the IgG class (MW about 150 kD) has been used for conjugation. The basic structure of the linker (marker) used (Bi(UE)$_{25}$-DSS) is given in FIG. 3. Instead of the ruthenium chelate complex this linker carries a biotinyl group (Bi-) and it has been modified to carry a DSS group at its C-terminal end.

Mode of Conjugation

Bi(UE)$_{25}$-DSS dissolved to a concentration of 15 mg/ml in DMSO is added to purified IgG of MAB<Ferritin>M-4.184 (10 mg/ml in 100 mM potassium phosphate buffer of pH 8.5) to result in a final molar ratio of 1:1 (IgG to linker). The reaction mixture is incubated for 60 minutes at 25° C. and conjugation stopped thereafter by addition of lysine to a final concentration of 10 mM.

The reaction product is dialyzed against a 20 mM potassium phosphate buffer of pH 7.5.

Purification of MAB<Ferritin>M-4.184-IgG-Bi((UE)$_{25}$-DSS)

Purification has been performed by Source 30 Q® chromatography. Elution has been performed by applying a salt gradient using 20 mM potassium phosphate (pH 6.5) as buffer (A) and 20 mM potassium phosphate with 1 M NaCl (pH 6.5) as buffer (B). The results obtained are given in FIG. 16. It is clear that by this procedure and by appropriate pooling immunoglobolin carrying only one linker (marker) (mono-biotinylated IgG) can be easily obtained.

LIST OF REFERENCES

Aslam, M. Dent, A. The preparation of protein-protein conjugates in "Bioconjugation" (1998) 216-363, London, McMillan B. W. Bycroft et al. (1993), J. Chem. Soc., Chem. Commun., 778

Engvall, E. and Perlman, P., Immunochemistry 8 (1971) 871-4

Merzouk A. et al., (1992) Tetrahedron Lett. 33, 477

Methods in Enzymology, Colowick S. P., Caplan N. O., Eds., Academic Press

Tijssen—in "Methods in Enzymology" (1992) Academic Press

Tijssen Laboratory techniques in "Macromolecule conjugation" (1985) 258-268

Wang S.-S., J. Am. Chem. Soc. 95 (1973) 1328 van Weemen, B. K. and Schuures A. H. W. M. (1971), FEBS letters 15, 232

PCT/EP 95/02921

EP 0 061 888

U.S. Pat. No. 5,958,783

WO 96/03409

WO 96/03423

WO 96/03651

WO 96/03652

WO 96/03657

The invention claimed is:

1. A process for production of a fraction of conjugates, each conjugate comprising a biomolecule and a linker and having a pre-defined ratio of biomolecule to linker so that the fraction has a pre-determined and uniform stoichiometry with respect to biomolecule and linker, wherein the biomolecule has at least two reactive sites, is selected from the group consisting of polypeptides, polysaccharides, and lipopolysaccharides, and, has a molecular weight of between 5 kD and 500 kD, and wherein the linker is a hydrophilic linker having a molecular weight between 1 kD and 15 kD and containing between 4 and 60 charged residues, the process comprising:

covalently coupling the biomolecule to the linker, thereby generating a mixture of coupling products comprising the conjugates having the pre-defined ratio of biomolecule to linker, fractionating by chromatography the mixture of coupling products, and collecting a fraction comprising the conjugates having the pre-defined ratio of biomolecule to linker, wherein said pre-defined ratio of biomolecule to linker is selected from the group consisting of 1:1, 1:2, 1:3, and 1:4.

2. The process of claim 1 wherein the charged residues are negatively charged.

3. The process of claim 1 wherein the charged residues are positively charged.

4. The process of claim 1 wherein the hydrophilic linker comprises 6 to 50 charged residues.

5. The process of claim 1 wherein the linker comprises a peptide backbone.

6. The process of claim 1 wherein the biomolecule is a polypeptide.

7. The process of claim 1 wherein the chromatographic fractionation is based on differences in apparent molecular weight of the coupling products.

8. The process of claim 7 wherein the linker has an apparent molecular weight between 20% and 500% of that of the biomolecule as determined using molecular sieve chromatography.

9. The process of claim 1 wherein the chromatographic fractionation is based on differences in charge of the coupling products.

10. The process of claim 1 wherein the pre-defined ratio of biomolecule to linker is 1:2.

11. The process of claim 1 wherein the pre-defined ratio of biomolecule to linker is 1:1.

12. The process of claim 1 wherein the linker comprises a β-alanine-glutamic acid peptide.

13. The process of claim 1 wherein the conjugate further comprises a detectable label.

14. The process of claim 1 wherein the conjugate further comprises a member of a bioaffinity binding pair.

* * * * *